(12) United States Patent
Zhou et al.

(10) Patent No.: US 9,487,809 B2
(45) Date of Patent: Nov. 8, 2016

(54) DECREASING LACTATE LEVEL AND INCREASING POLYPEPTIDE PRODUCTION BY DOWNREGULATING THE EXPRESSION OF LACTATE DEHYDROGENASE AND PYRUVATE DEHYDROGENASE KINASE

(71) Applicant: Genentech, Inc., South San Francisco, CA (US)

(72) Inventors: Meixia Zhou, Foster City, CA (US); Bradley Richard Snedecor, Portola Valley, CA (US); Chi Kin Domingos Ng, San Francisco, CA (US); Amy Shen, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 233 days.

(21) Appl. No.: 13/688,075

(22) Filed: Nov. 28, 2012

(65) Prior Publication Data

US 2013/0084605 A1 Apr. 4, 2013

Related U.S. Application Data

(63) Continuation of application No. PCT/US2011/038191, filed on May 26, 2011.

(60) Provisional application No. 61/349,727, filed on May 28, 2010.

(51) Int. Cl.
| C12P 21/00 | (2006.01) |
| A61K 48/00 | (2006.01) |
| C12N 15/85 | (2006.01) |
| C12N 15/113 | (2010.01) |
| C12N 15/11 | (2006.01) |
| C12N 1/38 | (2006.01) |

(52) U.S. Cl.
CPC ........... *C12P 21/00* (2013.01); *C12N 1/38* (2013.01); *C12N 15/111* (2013.01); *C12N 15/113* (2013.01); *C12N 15/85* (2013.01); *C12N 2310/14* (2013.01); *C12N 2320/00* (2013.01)

(58) Field of Classification Search
USPC ............ 435/6.1, 69.1, 91.1, 91.31, 455, 3, 435/320.1, 325, 326; 536/23.1, 24.5
See application file for complete search history.

(56) References Cited

U.S. PATENT DOCUMENTS

| RE30,985 E | 6/1982 | Cartaya |
| 4,515,893 A | 5/1985 | Kung et al. |
| 4,560,655 A | 12/1985 | Baker |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 5,091,313 A | 2/1992 | Chang |
| 5,122,469 A | 6/1992 | Mather et al. |
| 5,622,700 A | 4/1997 | Jardieu et al. |
| 5,672,347 A | 9/1997 | Aggarwal et al. |
| 5,693,762 A | 12/1997 | Queen et al. |
| 5,714,388 A | 2/1998 | Kusnetz |
| 5,721,108 A | 2/1998 | Robinson et al. |
| 5,726,856 A | 3/1998 | King, Jr. et al. |
| 5,736,137 A | 4/1998 | Anderson et al. |
| 2009/0209618 A1 | 8/2009 | Dang et al. |
| 2009/0215860 A1 | 8/2009 | Morris et al. |
| 2009/0325287 A1 | 12/2009 | Dorai et al. |

FOREIGN PATENT DOCUMENTS

| EP | 0 183 070 A2 | 6/1986 |
| EP | 0 183 070 A3 | 6/1986 |
| EP | 0 183 070 B1 | 6/1986 |
| EP | 0 244 234 A1 | 11/1987 |
| EP | 0 244 234 A3 | 11/1987 |
| EP | 0 244 234 B1 | 11/1987 |
| EP | 0 308 936 A2 | 3/1989 |
| EP | 0 308 936 A3 | 3/1989 |
| EP | 0 308 936 B1 | 3/1989 |
| EP | 0 402 226 A1 | 12/1990 |
| EP | 0 420 937 B1 | 11/1994 |
| WO | WO-87/00195 A1 | 1/1987 |
| WO | WO-90/03430 A1 | 4/1990 |
| WO | WO-91/00360 A1 | 1/1991 |
| WO | WO-92/20373 A1 | 11/1992 |
| WO | WO-93/04173 A1 | 3/1993 |
| WO | WO-93/08829 A1 | 5/1993 |
| WO | WO-93/16185 A1 | 8/1993 |
| WO | WO-95/19181 A1 | 7/1995 |

(Continued)

OTHER PUBLICATIONS

Chen et al (Biotech. & Bioeng., vol. 72, No. 1, pp. 55-61 (2001)).*
Jeong et al (Biochem. & Biophys. Res. Comm., vol. 289, pp. 1141-1149 (2001)).*
Kim et al Appl. Microbiol. Biotechnol., vol. 74, pp. 152-159 (2007)).*
Wigfield et al (Brit. J. Cancer, vol. 98, pp. 1975-1984 (2008)).*
Harris et al (Advan. Enzyme Regul., vol. 42, pp. 249-259 (2002)).*
Aruffo et al., "CD44 is the principal cell surface receptor for hyaluronate," Cell 61:1303-1313, (Jun. 29, 1990).

(Continued)

*Primary Examiner* — Jane Zara
(74) *Attorney, Agent, or Firm* — Morrison & Foerster LLP

(57) ABSTRACT

The present invention provides methods and compositions for reducing lactate production and increasing polypeptide production in cultured cells. In one aspect, the invention provides a method comprising culturing cells expressing a) a small interfering RNA (siRNA) specific for a lactate dehydrogenase (LDH) and b) an siRNA specific for a pyruvate dehydrogenase kinase (PDHK). In another aspect, the invention provides cultured cells or vectors comprising an siRNA specific for a LDH and an siRNA specific for a PDHK.

12 Claims, 12 Drawing Sheets

(56) References Cited

FOREIGN PATENT DOCUMENTS

| WO | WO-95/23865 A1 | 9/1995 |
|---|---|---|
| WO | WO-96/27011 A1 | 9/1996 |
| WO | WO-96/30046 A1 | 10/1996 |
| WO | WO-96/40210 A1 | 12/1996 |
| WO | WO-97/26912 A2 | 7/1997 |
| WO | WO-97/26912 A3 | 7/1997 |
| WO | WO-97/26912 C1 | 7/1997 |
| WO | WO-98/06248 A2 | 2/1998 |
| WO | WO-98/06248 A3 | 2/1998 |
| WO | WO-98/23761 A1 | 6/1998 |
| WO | WO-98/45331 A2 | 10/1998 |
| WO | WO-98/45331 A3 | 10/1998 |
| WO | WO-98/51793 A1 | 11/1998 |
| WO | WO-00/78348 A1 | 12/1998 |
| WO | WO-01/00245 A2 | 1/2001 |
| WO | WO-01/00245 A3 | 1/2001 |
| WO | WO-01/40309 A2 | 6/2001 |
| WO | WO-01/40309 A3 | 6/2001 |
| WO | WO-02/04598 A2 | 1/2002 |
| WO | WO-02/04598 A3 | 1/2002 |
| WO | WO-2009/152413 A1 | 12/2009 |
| WO | WO-2010/031074 A2 | 3/2010 |
| WO | WO-2010/031074 A3 | 3/2010 |

OTHER PUBLICATIONS

Barnes et al., "Methods for growth of cultured cells in serum-free medium," *Anal. Biochem.* 102:255-270, (1980).

Baumgart et al., "L-lactate dehydrogenase $A_4$- and $A_3B$ isoforms are bona fide peroxisomal enzymes in rat liver. Evidence for involvement in intraperoxisomal NADH reoxidation," *J. Biol. Chem.* 27(7):3846-3855, (Feb. 1997).

Berg et al. "Bispecific antibodies that mediate killing of cells infected with human immunodeficiency virus of any strain," *Proc. Natl. Acad. Sci. USA* 88:4723-4727 (Jun. 1991).

Bowton-Kinley et al., "Evidence for existence of tissue-specific regulation of the mammalian pyruvate dehydrogenase complex," *Biochem. J.* 329(Pt. 1):191-196, (Jan. 1998).

Brennan et al. "Preparation of bispecific antibodies by chemical recombination of monoclonal immunoglobulin $G_1$ fragments," *Science* 229:81-83, (Jul. 5, 1985).

Brodeur Chapter 4 in Inc., New York, et al., "Mouse-human myeloma partners for the production of heterohybridomas," Chapter 4 in *Monoclonal Antibody Production Techniques and Applications*, Marcel Dekker, Inc., New York, New York, pp. 51-63, (1987).

Brüggermann et al., "Designer mice: The production of human antibody repertoires in transgenic animals," *Year in Immuno.* 7:33-40, (1993).

Carter et al., High level *Escherichia coli* expression and production of a bivalent humanized antibody fragment, *Bio/Technology* 10:163-167 (Feb. 1992).

Carter et al. "Humanization of an antip185$^{HER2}$ antibody for human cancer therapy," *Proc. Natl. Acad. Sci. USA* 89:4285-4289 (May 1992).

Ceriani et al. "Biological activity of two humanized antibodies against two different breast cancer antigens and comparison to their original murine forms," *Cancer Res.* 55(23):5852s-5856s (Dec. 1, 1995).

Chamow et al. "A humanized, bispecific immunoadhesin-antibody that retargets CD3$^+$ effectors to kill HIV-1-infected cells," *J. Immunol.* 153:4268-4280, (1994).

Chothia et al., "Canonical structures for the hypervariable regions of immunoglobulins," *J. Mol. Biol.* 196:901-917, (1987).

Choy et al., "Percentage of anti-cd4 monoclonal antibody-coated lymphocytes in the rheumatoid joint is associated with clinical improvements," *Arthritis Rheum.* 39(1):52-56, (Jan. 1996).

Clackson et al., "Making antibody fragments using phage display libraries," *Nature* 352:624-628, (Aug. 15, 1991).

Dhainaut et al., "CDP571, a humanized antibody to human tumor necrosis factor-α: Safety, pharmacokinetics, immune response, and influence of the antibody on cytokine concentrations in patients with septic shock," *Crit. Care Med.* 23(9):1461-1469, (Sep. 1995).

Dietl et al., "Lactic acid and acidification inhibit TNF secretion and glycolysis of human monocytes," *J. Immunol.* 184(3):1200-1209, (Feb. 1, 2010).

Duchosal et al., "Immunization of hu-PBL-SCID mice and the rescue of human monoclonal Fab fragments through combinatorial libraries," *Nature* 355:258-262, (Jan. 16, 1992).

Ellis et al., "Engineered anti-cd38 monoclonal antibodies for immunotherapy of multiple myeloma," *J. Immunol.* 155(2):925-937, (1995).

Goding., "Production of monoclonal antibodies," Chapter 3 in *Monoclonal Antibodies: Principles and Practice*, Academic Press, London, England, pp. 59-103. (1983).

Graham et al. "Characteristics of a human cell line transformed by DNA from human adenovirus type 5," *J. Gen Virol.* 36:59-72, (1977).

Graziano et al., "Construction and characterization of a humanized anti-γ-lg receptor type I (FcγRI) monoclonal antibody," *J. Immunol.* 155(10):4996-5002, (1995).

Gruber et al., "Efficient tumor cell lysis mediated by a bispecific single chain antibody expressed in *Escherichia coli*," *J. Immunol.* 152:5368-5374, (1994).

Ham et al., "Media and growth requirements," *Meth. Enz.* 58:44-93, (1979).

Holliger et al. "Diabodies: Small bivalent and bispecific antibody fragments," *Proc. Natl. Acad. Sci. USA* 90:6444-6448, (Jul. 1993).

Hoogenboom et al., "By-passing Immunisation. Human antibodies from synthetic repertoires of germline $V_H$ gene segments rearranged in Vitro," *J. Mol. Biol.* 227:381-388, (1991).

Hoogenboom et al., "Construction and expression of antibody-tumor necrosis factor fusion proteins," *Mol. Immunol.* 28(9):1027-1037, (1991).

Hourmant et al., Administration of an anti-CD11a monoclonal antibody in recipients of kidney transplantation, *Transplantation* 58:377-380 ,(Aug. 1994).

International Search Report mailed on Jan. 18, 2012, for PCT Application No. PCT/US11/38191, filed on May 26, 2011, one page.

Jakobovits et al., "Analysis of homozygous mutant chimeric mice: Deletion of the immunoglobulin heavy-chain joining region blocks B-cell development and antibody production," *Proc. Natl. Acad. Sci. USA* 90:2551-2555, (Mar. 1993).

Jakobovitis et al., "Germ-line transmission and expression of a human-derived yeast artificial chromosome," *Nature* 362:255-258, (Mar. 18, 1993).

Jones et al., "Replacing the complementarity-determining regions in a human antibody with those from a mouse," *Nature* 321:522-525, (May 29, 1986).

Jurcic et al., "Radiolabled anti-CD33 monoclonal antibody M195 for myeloid leukemias," *Cancer Res.* 55(23 Suppl.):5908s-5910s, (Dec. 1, 1995).

Juweid et al., "Treatment of non-hodgkin's lymphoma with radiolabeled murine, chimeric, or humanized LL2, an anti-CD22 monoclonal antibody," *Cancer Res.* 55(23 Suppl.):5899s-5907s, (Dec. 1, 1995).

Kim et al., "The vascular endothelial growth factor proteins: Growth factor proteins: Identification of biologically relevant regions by neutralizing monoclonal antibodies," *Growth Factors* 7:53-64, (1992).

Kim et al., "Down-regulation of lactate dehydrogenase-A by siRNAs for reduced lactic acid formation of Chinese hamster ovary cells producing thrombopoietin," *Appl. Microbiol. Biotechnol.* 74(1):152-159, (Nov. 4, 2006).

Köhler et al., "Continuous cultures of fused cells secreting antibody of predefined specificity," *Nature* 256:495-497, (1975).

Kostelny et al., "Formation of a bispecific antibody by the use of leucine zippers," *J. Immunol.* 148(5):1547-1553, (Mar. 1, 1992).

Kozbor et al. "A human hybrid myeloma for production of human monoclonal antibodies," *J. Immunol.* 133(6):3001-3005, (Dec. 1984).

(56) References Cited

OTHER PUBLICATIONS

Kuystermans et al. "Using cell engineering and omic tools for the improvement of cell culture processes," *Cytotechnology* 53(1-3):3-22, (Apr. 2007, e-pub. Feb. 24, 2007).
Li et al., "Evolutionary relationships of vertebrate lactate dehydrogenase isozymes $A_4$ (muscle), $B_4$ (heart), and $C_4$ (testis)," *J. Biol. Chem.* 258(11):7029-7032, (Jun. 10, 1983).
Lindmark et al., "Binding of immunoglobulins to protein A and immunoglobulin levels in mammalian sera," *J. Immunol. Meth.* 62:1-13, (1983).
Litton et al., "Antibody-targeted superantigen therapy induces tumor-infiltrating lymphocytes, excessive cytokine production, and apoptosis in human colon carcinoma," *Eur. J. Immunol.* 26(1):1-9, (1996).
Liu et al., "Lactate inhibits lipolysis in fat cells through activation of an orphan G-protein-coupled receptor, GPR81," *J. Biol. Chem.* 284(5):2811-2822, (Jan. 30, 2009).
Lorenz et al., "In vivo blockade of TNF-α by Intravenous infusion of a chimeric monoclonal TNF-α antibody in patients with rheumatoid arthritis," *J. Immunol.* 156(4):1646-1653, (1996).
Lu et al., "Induction of Pyruvate Dehydrogenase Kinase-3 by Hypoxia-inducible Factor-1 Promotes Metabolic Switch and Drug Resistance," *J. Biol. Chem.* 283(42):28106-28114, (Oct. 17, 2008).
Marks et al., "By-passing Immunization. Human antibodies from V-gene libraries displayed on phage," *J. Mol. Biol.* 222:581-597, (1991).
Marks et al., "By-passing immunization: Building high affinity human antibodies by chain shuffling," *Bio/Technology* 10:779-783 (Jul. 1992).
Mather., "Establishment and characterization of two distinct mouse testicular epithelial cell lines," *Biol. Reproof.* 23:243-251, (1980).
Mather et al., "Culture of testicular cells in hormone-supplemented serum-free medium," *Annals N.Y. Acad. Sci.* 383:44-68, (1982).
Mathupala et al., "Hexokinase-2 bound to mitochondria: Cancer's stygian link to the 'Warburg effect' and a pivotal target for effective therapy," *Seminars in Cancer Biology* 19:17-24, 17 pages, (Feb. 2009).
McCafferty et al., "Phage antibodies: filamentous phage displaying antibody variable domains," *Nature* 348:552-554, (Dec. 6, 1990).
Milstein et al., "Hybrid hybridomas and their use in immunohistochemistry," *Nature* 305:537-540, (Oct. 6, 1983).
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *Journal of Biochemical and Biophysical Methods* 24:107-117, (1992).
Morrison et al., "Chimeric human antibody molecules: Mouse antigen binding domains with human constant region domains," *Proc. Natl. Acad. Sci. USA* 81:6851-6855, (Nov. 1984).
O'Callaghan et al., Systems biotechnology of mammalian cell factories, *Brief Funct. Genomic Proteomic* 7(2):95-110, (Mar. 2008).
Patel et al., "Regulation of mammalian pyruvate dehydrogenase complex by phosphorylation: complexity of multiple phosphorylation sites and kinases," *Exp. Mol. Med.* 33(4):191-197, (Dec. 2001).
Presta., "Antibody engineering," *Curr. Op. Struct. Biol.* 2:593-596, (1992).
Presta et al. "Humanization of an antibody directed against IgE," *J. Immunol.* 151(5):2623-2632, (Sep. 1, 1993).
Richman et al., "Radioimmunotherapy for breast cancer using escalating fractionated doses of $^{131}$I-labeled chimeric L6 antibody with peripheral blood progenitor Cell," *Cancer Res.* 55(23 Suppl.): 5916s-5920s, (Dec. 1, 1995).
Riechmann et al., "Reshaping human antibodies for therapy," *Nature* 332:323-329, (Mar. 24, 1988).
Rutz et al., "Towards in vivo application of RNA interference—new toys, old problems," *Arthritis Research and Therapy* 6(2):78-85 (2004, e-pub. Mar. 10, 2004).

Samuvel et al., "Lactate boosts TLR4 signaling and NF-κB pathway-mediated gene transcription in macrophages via monocarboxylate transporters and MD-2 up-regulation," *J. Immunol.* 182(4):2476-2484, (Feb. 2009).
Shalaby et al., "Development of humanized bispecific antibodies reactive with cytotoxic lymphocytes and tumor cells overexpressing the *HER2* protooncogene," *J. Exp. Med.* 175:217-225, (Jan. 1, 1992).
Sharkey et al., Evaluation of a complementarity-determining region-grafted (humanized) anti-carcinoembryonic antigen monoclonal antibodies, *Cancer Res.* 55(23 Suppl.):5935s-5945s, (Dec. 1, 1995).
Sims et al., "A humanized cd18 antibody can block function without cell destruction," *J. Immunol.* 151(4):2296-2308, (Aug. 15, 1993).
Skory., "Isolation and expression of lactate dehydrogenase genes from *Rhizopus oryzae*," *Appl. Envion. Microbiol.* 66(6):2343-2348, (Jun. 2000).
St. John et al., "Immunologic therapy for ARDS, septic shock, and multiple-organ failure," *Chest* 103:932-943, (1993).
Stamenkovic et al., "The B lymphocyte adhesion molecule CD22 interacts with leukocyte common antigen CD45RO on t cells and α2-6 Sialyltransferase, CD75, on B cells," *Cell* 66:1133-1144, (Sep. 20, 1991).
Traunecker et al., "Bispecific single chain molecules (Janusins) target cytotoxic lymphocytes on HIV infected cells," *EMBO J.* 10(12):3655-3659, (1991).
Tutt et al., "Trispecific F(ab')3 derivatives that use cooperative signaling via the tcr/cd3 complex and cd2 to activate and redirect resting cytotoxic t cells," *J. Immunol.* 147(1):60-69, (Jul. 1, 1991).
Urlaub et al., "Isolation of Chinese hamster cell mutations deficient in dihydrofolate reductase activity," *Proc. Natl. Acad. Sci. USA* 77(7):4216-4220, (Jul. 1980).
Vaughan et al., "Human antibodies with sub-nanomolar affinities isolated from a large non-immunized phage display library," *Nature Biotech.* 14:309-314, (Mar. 1996).
Verhoeyen et al., "Reshaping human antibodies: Grafting an antilysozyme activity," *Science* 239:1534-1536, (1988).
Waterhouse et al., Combinatorial infection and in vivo recombination: a strategy for making large phage antibody repertoires, *Nuc. Acids Res.* 21(9):2265-2266, (1993).
Wigfield et al., "PDK-1 regulates lactate production in hypoxia and is associated with poor prognosis in head and neck squamous cancer," *British Journal of Cancer* 98:1975-1984, (Jun. 10, 2008).
Written Opinion mailed on Jan. 18, 2012, for PCT Application No. PCT/US11/38191, filed on May 26, 2011, ten pages.
Zapata et al., "Engineering linear F9ab')$_2$ fragments for efficient production in *Escherichia coli* and enhanced antiproliferative activity," *Protein Eng.* 8(10):1057-1062, (1995).
Zhou et al., "Decreasing lactate level and increasing antibody production in Chinese hamster ovary cells (CHO) by reducing the expression of lactate dehydrogenase and pyruvate dehydrogenase kinases," *Journal of Biotechnology* 153:27-34, (2011, e-pub. Mar. 8, 2011).
Chen et al., "Engineering of a mammalian cell line for reduction of lactate formation and high monoclonal antibody production," *Biotechnol. Bioeng.* 72(1):55-61, (Jan. 5, 2001).
Cruz et al., "Effects of ammonia and lactate on growth, metabolism, and productivity of BHK cells," *Enzyme Microb. Technol.* 27(1-2):43-52, (Jul. 1, 2000).
Elbashier et al., "Analysis of gene function in somatic mammalian cells using small interfering RNAs," *Methods* 26:199-213, (2002).
Glacken et al., "Mathematical descriptions of hybridoma culture kinetics: I. Initial metabolic rates," *Biotechol. Bioeng.* 66(3):171-179, (1988).
Harris et al., (2002). "Regulation of the activity of the pyruvate dehydrogenase complex," *Adv. Enzyme Regul.* 42:249-259, (2002).
Holness et al. "Regulation of pyruvate dehydrogenase complex activity by reversible phosphorylation," *Biochem Soc. Trans.* 31(Pt. 6):1143-51, (Dec. 2003).
Irani et al., "Improvement of the primary metabolism of cell cultures by introducing a new cytoplasmic pyruvate carboxylase reaction," *Biotechnol. Bioeng.* 66(4):238-246, (1999).

(56) References Cited

OTHER PUBLICATIONS

Jeong et al., "Blocking of acidosis-mediated apoptosis by a reduction of lactate dehydrogenase activity through antisense mRNA expression," *Biochem. Biophys Res. Commun.* 289(5):1141-1149, (Dec. 21, 2001).
Langheinrich et al., "Control of pH in large-scale, free suspension animal cell bioreactors: alkali addition and pH excursions," *Biotechnol. Bioeng.* 66(3):171-179, (1999).
Lao et al., "Effects of ammonium and lactate on growth and metabolism of a recombinant Chinese hamster ovary cell culture," *Biotechnol Prog.* 13(5):688-691, (Sep.-Oct. 1997).
Rao et al., "siRNA vs. shRNA: Similarities and Differences," *Advanced Drug Delivery Reviews* 61:746-759, (2009).
Read et al., "Structural basis for altered activity of M- and H-isozyme forms of human lactate dehydrogenase," *Proteins* 43(2)175-185, (May 2001).
Roche et al., "Pyruvate dehydrogenase kinase regulatory mechanisms and inhibition in treating diabetes, heart ischemia, and cancer," *Cell Mol. Life Sci.* 64(7-8):830-849, (Apr. 2007).
Stoppa et al., "Anti-LFA1 monoclonal antibody (25.3) for treatment of steroid-resistant grade III-IV acute graft-versus-host disease," *Transplant Intl.* 4:3-7, (1991).
Fahrner et al., "Performance comparison of protein A affinity-chromatography sorbents for purifying recombinant monoclonal antibodies," *Biotechnol. Appl. Biochem.* 30(Part 2):121-128, (Oct. 1999).
Davis et al., "Lymphoid Cell Functions During Copper Deficiency," *Nutrition Research* 7:211-222, (1987).
Gu et al., "Lactate and Pyruvate Levels in Blood and Cerebrospinal Fluid in Patients with Menkes Disease," *The Journal of Pediatrics* 164:890-894, (2014).
Luo et al., "Comparative Metabolite Analysis to Understand Lactate Metabolism Shift in Chinese Hamster Ovary Cell Culture Process," *Biotechnology and Bioengineering* 109(1):146-156, (Jan. 2012).
Patel et al., "Regulation of the Pyruvae Dehydrogenase Complex," *Biochemical Society Transactions* 34(2):217-222, (2006).
Wu et al. "RNA Interference Technology to 1-46 Improve Recombinant Protein Production in Chinese hamster ovary cells," *Biotechnology Advances* 27(4):417-422, (Jul. 1, 2009).
Zagari et al., "Lactate Metabolism Shift in CHO Cell Culture: The Role of Mitochondrial Oxidative Activity," *New Biotechnology* 30(2):238-245, (Jan. 2013).
Supplemental European Search Report mailed on Jun. 3, 2014, for European Patent Application No. 11787435.4, filed on May 26, 2011, 7 pages.

\* cited by examiner

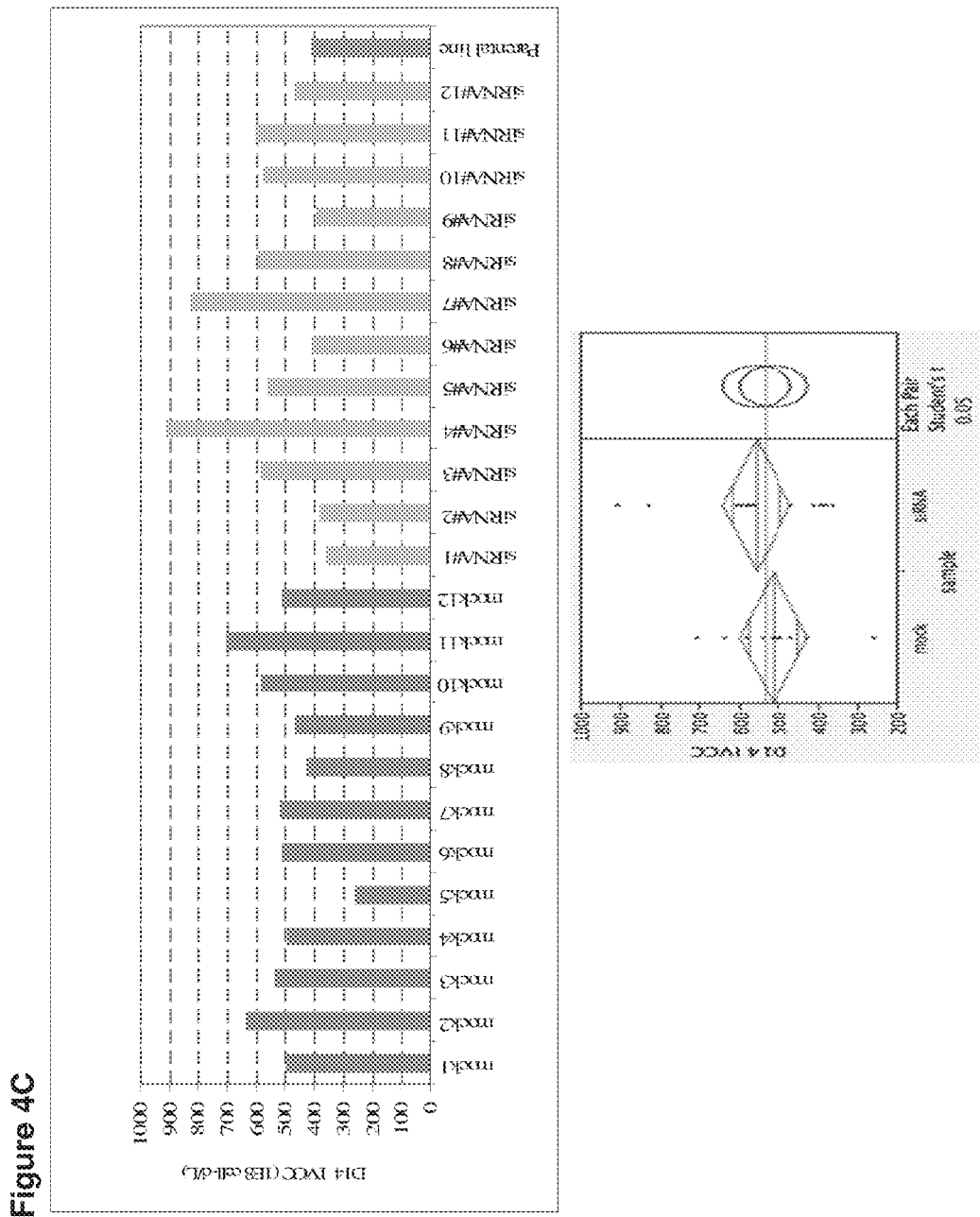

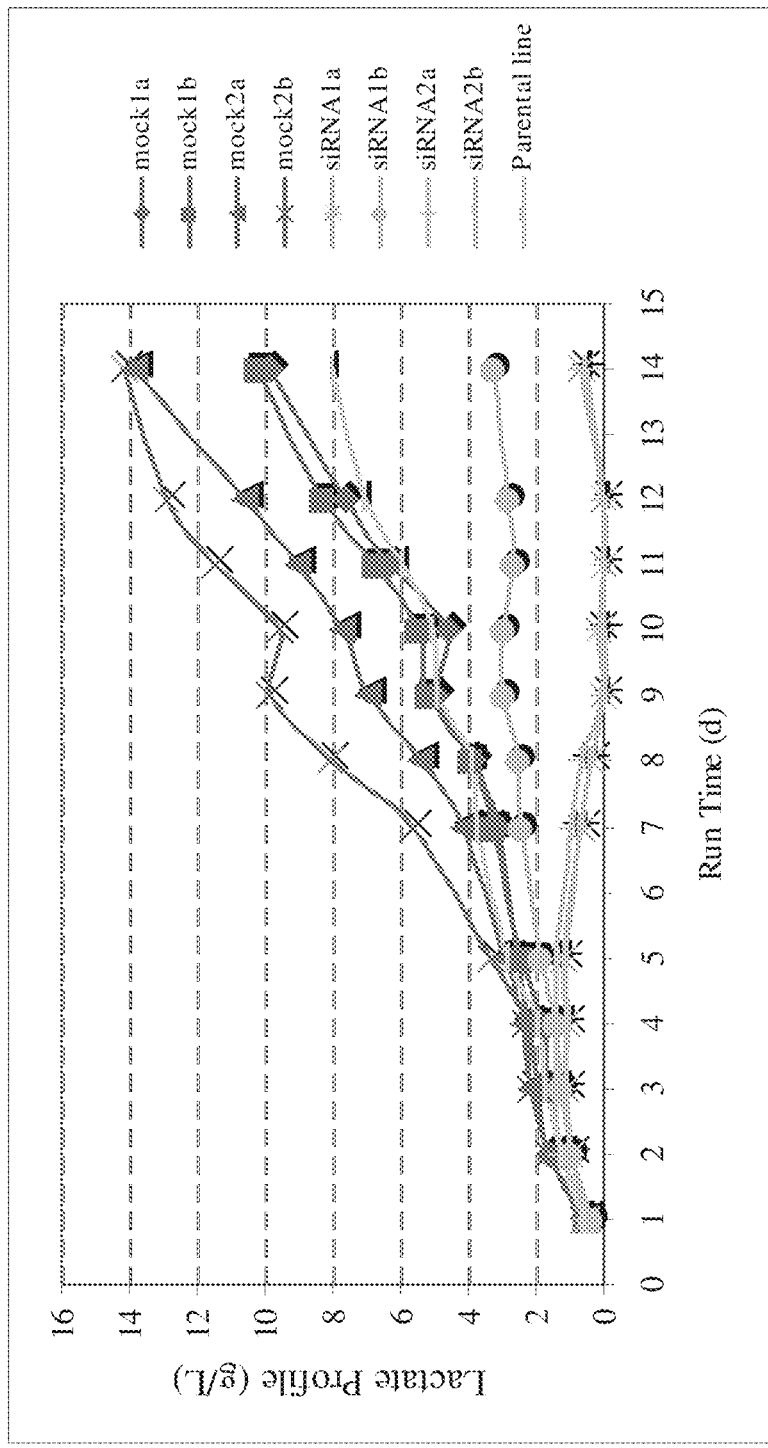

DECREASING LACTATE LEVEL AND INCREASING POLYPEPTIDE PRODUCTION BY DOWNREGULATING THE EXPRESSION OF LACTATE DEHYDROGENASE AND PYRUVATE DEHYDROGENASE KINASE

CROSS-REFERENCE TO RELATED APPLICATIONS

This application is a continuation of International Patent Application No. PCT/US2011/038191, filed May 26, 2011; which claims priority benefit to U.S. Provisional Patent Application No. 61/349,727 filed May 28, 2010, the content of each of which is hereby incorporated herein by reference in its entirety.

SEQUENCE LISTING

The instant application contains a Sequence Listing submitted via EFS-Web and hereby incorporated by reference in its entirety. Said ASCII copy, created on Nov. 15, 2012, is named 146392007800, and is 3.83 bytes in size.

FIELD OF THE INVENTION

The field of this invention relates generally to methods and compositions for reducing lactate production and increasing polypeptide production in cultured cells.

BACKGROUND OF THE INVENTION

Biopharmaceutical market is growing rapidly, and the industry is projected to reach $70 billion dollars by year 2010. See Genetic Engineering in Livestock: New Applications and Interdisciplinary Perspectives (Engelhard et al., 2009) Springer Berlin Heidelberg. Given the increase in demand in therapeutic proteins and the increase in competitions in market sharing among companies, there is a need in improving technologies to achieve better productivity in therapeutic proteins. Towards this goal, different approaches, such as host cell engineering, have been explored. See Kuystermans et al., *Cytotechnology* 53(1-3): 3-22 (2007); and O'Callaghan and James, *Brief Funct. Genomic Proteomic* 7(2):95-110 (2008). Cultured cells, such as Chinese Hamster Ovary (CHO) cells, are widely used to produce therapeutic proteins. For example, pH-controlled fed-batch bioreactor culture has been used widely to produce recombinant monoclonal antibodies. Langheinrich and Nienow, *Biotechnol. Bioeng.* 66(3):171-9 (1999). Lactate is one of the main accumulated waste products during fed-batch culture, and it has been shown to inhibit cell growth and protein production. See Glacken et al., *Biotechnol. Bioeng.* 32:491-506 (1988); and Lao and Toth, *Biotechnol. Prog.* 13:688-691 (1997). This in turn leads to an increase in the amount of alkali needed for adding into the culture medium to control the pH. Dietl et al., *J. Immunol.* 184(3):1200-9 (2010); Langheinrich and Nienow, *Biotechnol. Bioeng,* 66(3):171-9 (1999). Increased addition of alkali to the cell culture medium for maintaining the pH can result in an increase in osmolality, and this increase can lead to cell growth inhibition and decreased antibody productivity. Cruz et al., *Enzyme Microb. Technol.* 27(1-2):43-52 (2000); Iran et al., *Biotechnol. Bioeng.* 66:238-246 (1999). Hence, reducing the lactate level is desired for the development of polypeptide or a higher titer antibody production process.

There are many factors that can influence lactate production in cell culture, such as controlling the pyruvate level. See Liu et al., *J. Biol. Chem.,* 284(5):2811-22 (2009); and Samuvel et al., *J. of Immunol.* 182(4):2476-84 (2009). Pyruvate is the substrate for the enzymes pyruvate dehydrogenase (PDH) and lactate dehydrogenase (LDH).

The PDH complex is a multi-enzyme unit consisting of three catalytic enzymes, E1, E2, and E3. Patel and Korotchkina, *Exp. Mol. Med.* 33(4):191-7 (2001). This complex catalyzes the rate-limiting conversion reaction in converting from pyruvate to acetyl-CoA, which is the entry point of tricarboxylic acid (TCA) cycle. The activity of PDH is regulated by the enzymes pyruvate dehydrogenase kinases (PDHK(s)) and pyruvate dehydrogenase phosphatases (PDHPs). PDHKs phosphorylate PDH to suppress its enzymatic activity, whereas PDHP dephosphorylate and thus activate PDH. See Patel and Korotchkina, *Exp. Mol. Med.* 33(4):191-7 (2001); Roche and Hiromasa, *Cell Mol. Life. Sci.* 64(7-8):830-49 (2007); Holness and Sugden, *Biochemical Society Transactions,* 31:1143-1151 (2003). There are four isotypes of PDHK in mammalian cells (PDHK1, PDHK2, PDHK3, and PDHK4) with tissue specific distributions. See Harris et al., *Adv. Enzyme Regul.* 42:249-59 (2002); and Bowker-Kinley et al., *Biochem. J.* 329(1):191-6 (1998).

LDH directly catalyzes the interconversion of pyruvate and lactate with concurrent interconversion of NADH and NAD+. In mammalian cells, LDHs exist as either homo- or heterotetramers consisting mostly A and B subunits (or H and M subunits, respectively) encoded by LDHa and LDHb genes, and sometimes homotetramers of C subunit encoded by LDHc genes. See Baumgart et al., *J. Biol. Chem.* 271 (7):3846-55 (1996); Li et al., *J. Biol. Chem.* 258(11):7029-32 (1983); Skory C. D., *Appl. Environ. Microbiol.* 66(6): 2343-8 (2000); and Read et al., *Proteins* 43(2):175-185 (2001). For example, in CHO cells, LDH isotypes have been shown to be intermediates of the A3B and A2B2 tetramer. Jeong et al., *Biochem. Biophys. Res. Commun.* 289(5): 1141-9 (2001). Previous studies have shown that downregulating LDHa in CHO cells by disrupting the gene via homologous recombination (Chen et al., *Biotechnol. Bioeng.* 72(1):55-61 (2001)), antisense technology (Jeong et al., *Biochem. Biophys. Res. Commun.* 289(5):1141-9 (2001)), or small or short interfering RNA (siRNA) (Kim and Lee, *Appl. Microbiol. Biotechnol.* 74(1):152-9 (2007)) can reduce lactate level, but did not achieve appreciable improvement in protein productivity. For example, in the case of LDHa specific siRNA, even though there was reportedly a 45-79% reduction in lactate level, there was no significant improvement in Specific Productivity (Qp) and product (antibody) titer, suggesting that knocking down LDHa alone in CHO cells is not sufficient to improve Qp and product yield efficiently. Thus, more efficient methods for reducing lactate production are needed for achieving a better therapeutic polypeptide production.

All publications, patents, and patent applications cited herein are hereby incorporated by reference herein in their entirety for all purposes to the same extent as if each individual publication, patent, and patent application were specifically and individually indicated to be so incorporated by reference.

BRIEF SUMMARY OF THE INVENTION

The present invention provides methods and compositions for reducing lactate production and increasing polypeptide production in cultured cells. The inventors have discovered that concomitant downregulation of a LDH and PDHKs via siRNAs in cultured cells expressing polypeptides (e.g., antibodies) decreased lactate level, lactate production rate, and osmolality, and increased specific polypeptide productivity (e.g., Specific Productivity) and polypeptide production (e.g., productivity). Further, these cultured cells with downregulated LDH and PDHKs exhibited no negative impact on cell growth, cell viabilities, and the quality of polypeptides produced.

In one aspect, the invention provides a method for reducing lactate production in cultured cells, the method comprising culturing cells expressing a) a small interfering RNA (siRNA) specific for a lactate dehydrogenase (LDH) and b) an siRNA specific for a pyruvate dehydrogenase kinase (PDHK).

In another aspect, the invention provides cells in culture comprising a) an siRNA specific for a LDH and an siRNA specific for a PDHK.

In some embodiments, the cultured cells further express an siRNA specific for a second PDHK. In some embodiments, the cultured cells further express an siRNA specific for a third PDHK. In some embodiments, the cultured cells further express an siRNA specific for a fourth PDHK.

In another aspect, the invention provides a method for reducing lactate production in cultured cells, the method comprising culturing cells comprising a first heterologous nucleic acid sequence encoding a small interfering RNA (siRNA) specific for a lactate dehydrogenase (LDH) and a second heterologous nucleic acid sequence encoding an siRNA specific for a pyruvate dehydrogenase kinase (PDHK), wherein the first heterologous nucleic acid sequence is operably linked to a first promoter, and wherein the second heterologous nucleic acid sequence is operably linked to a second promoter.

In another aspect, the invention provides cells in culture comprising a first heterologous nucleic acid sequence encoding a first siRNA specific for a LDH and a second heterologous nucleic acid sequence encoding a second siRNA specific for a PDHK, wherein the first heterologous nucleic acid sequence is operably linked to a first promoter, and wherein the second heterologous nucleic acid sequence is operably linked to a second promoter.

In some embodiments, the cells further comprise a third heterologous nucleic acid sequence encoding an siRNA specific for a second PDHK and wherein the third heterologous nucleic acid sequence is operably linked to a third promoter. In some embodiments, the cells further comprise a fourth heterologous nucleic acid sequence encoding an siRNA specific for a third PDHK and wherein the fourth heterologous nucleic acid sequence is operably linked to a fourth promoter. In some embodiments, the cells further comprise a fifth heterologous nucleic acid sequence encoding an siRNA specific for a fifth PDHK and wherein the fifth heterologous nucleic acid sequence is operably linked to a fifth promoter.

In some embodiments, the LDH is LDHa, LDHb, or LDHc.

In some embodiments, the PDHK is selected from the group consisting of PDHK1, PDHK2, PDHK3, and PDHK4. In some embodiments, the PDHK is selected from the group consisting of PDHK1, PDHK2, and PDHK3. In some embodiments, the PDHK is selected from the group consisting of PDHK1 and PDHK2. In some embodiments, the PDHK is selected from the group consisting of PDHK1 and PDHK3. In some embodiments, the PDHK is selected from the group consisting of PDHK2 and PDHK3.

In some embodiments, the method for reducing lactate production in cultured cells comprises culturing cells comprising a first heterologous nucleic acid sequence encoding an siRNA specific for a lactate dehydrogenase (LDH) and a second, third, and fourth heterologous nucleic acid sequences encoding three different siRNAs specific for a first, second, and third PDHKs, wherein the first heterologous nucleic acid sequence is operably linked to a first promoter, and wherein the second, third, and fourth heterologous nucleic acid sequences are operably linked to a second, third, and fourth promoters, respectively. In some embodiments, the LDH is LDHa, wherein the first PDHK is PDHK1, the second PDHK is PDHK2, and the third PDHK is PDHK3.

In some embodiments, the cells in culture comprises a first heterologous nucleic acid sequence encoding a first siRNA specific for a LDH and a second, third, and fourth heterologous nucleic acid sequences encoding three different siRNAs specific for a first, second, and third PDHKs, wherein the first heterologous nucleic acid sequence is operably linked to a first promoter, and wherein the second, third, and fourth heterologous nucleic acid sequences are operably linked to a second, third, and fourth promoters, respectively. In some embodiments, the LDH is LDHa, wherein the first PDHK is PDHK1, the second PDHK is PDHK2, and the third PDHK is PDHK3.

In some embodiments, the cultured cells produce a heterologous polypeptide. In some embodiments, the heterologous polypeptide is an antibody.

In some embodiments, the lactate synthesis rate of the cultured cells is lower than the lactate consumption rate. In some embodiments, the average lactate production rate is less than about negative 0.02 mg/$10^6$ cells/day.

In some embodiments, the cultured cells containing siRNAs specific for the LDH and PDHK(s) has an osmolality at less than about 300 mOsm.

In some embodiments, the cultured cells have a Specific Productivity (Qp) of at least about 75% higher than cultured cells without the heterologous nucleic acid sequence comprising the PDHK(s) and the LDH.

In some embodiments, the cultured cells have a Specific Productivity (Qp) of at least about 75% higher than cultured cells without the siRNAs specific for the LDH and PDHK(s).

In some embodiments, the cultured cells have a polypeptide productivity (e.g., antibody productivity or titer in g/L) of about 10% to about 800% higher than cultured cells without the heterologous nucleic acid sequence comprising the PDHK(s) and the LDH. In some embodiments, the cultured cells have a polypeptide productivity of about 55% higher than cultured cells without the heterologous nucleic acid sequence comprising the PDHK(s) and the LDH. In some embodiments, the cultured cells have of a polypeptide productivity of at least about 68% higher than cultured cells without the heterologous nucleic acid sequence comprising the PDHK(s) and the LDH.

In some embodiments, the cultured cells have a polypeptide productivity of about 10% to about 800% higher than cultured cells without the siRNAs specific for the PDHK(s) and the LDH. In some embodiments, the cultured cells have a polypeptide productivity of about 55% higher than cultured cells without the siRNAs specific for the PDHK(s) and the LDH. In some embodiments, the cultured cells have a polypeptide productivity of at least about 68% higher than cultured cells without the siRNAs specific for the PDHK(s) and the LDH.

In some embodiments, the cultured cells are mammalian cells. In some embodiments, the cultured cells are non-mammalian cells.

In another aspect, the invention provides a method of silencing or down-regulating LDH and PDHK transcription in a cultured cell comprising: introducing into the cell a vector comprising a first heterologous nucleic acid sequence encoding a siRNA specific for the LDH and a second heterologous nucleic acid sequence encoding an siRNA specific for the PDHK, wherein the first heterologous nucleic acid sequence is operably linked to a first promoter, and wherein the second heterologous nucleic acid sequence is operably linked to a second promoter, wherein the siRNAs are expressed, thereby silencing or down-regulating gene transcription of the LDH and the PDHK.

In another aspect, the invention provides a method of making a cell that exhibits decreased lactate production in culture, comprising introducing into the cell a vector comprising a first heterologous nucleic acid sequence encoding a siRNA specific for the LDH and a second heterologous nucleic acid sequence encoding an siRNA specific for the PDHK, wherein the first heterologous nucleic acid sequence is operably linked to a first promoter, and wherein the second heterologous nucleic acid sequence is operably linked to a second promoter.

In another aspect, the invention provides a vector comprising a first heterologous nucleic acid sequence encoding a small interfering RNA (siRNA) specific for a lactate dehydrogenase (LDH) and a second heterologous nucleic acid sequence encoding an siRNA specific for a pyruvate dehydrogenase kinase (PDHK), wherein the first heterologous nucleic acid sequence is operably linked to a first promoter, and wherein the second heterologous nucleic acid sequence is operably linked to a second promoter.

DETAILED DESCRIPTION OF THE INVENTION

Figure 1:
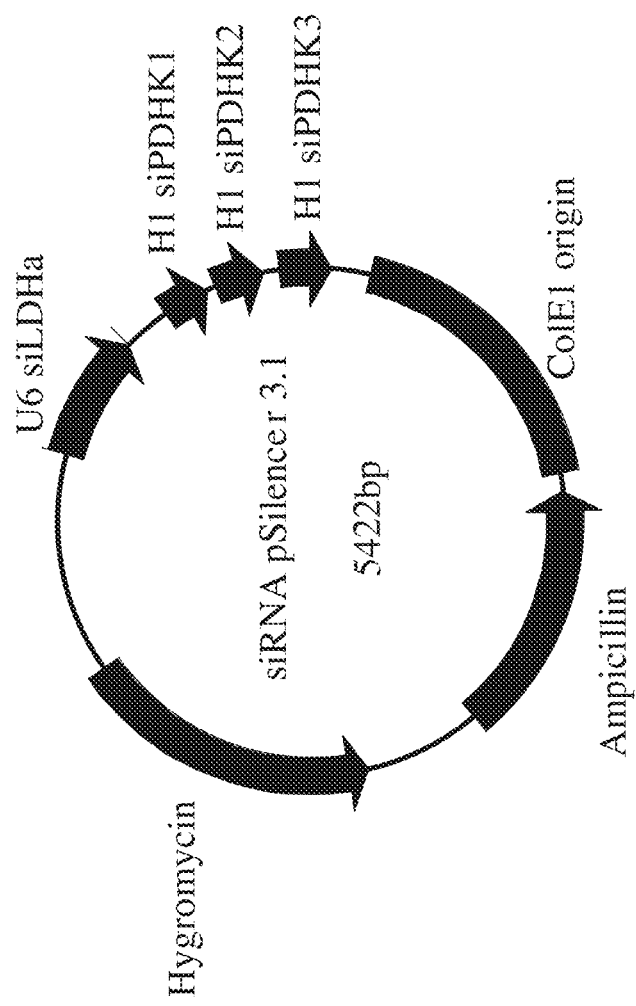
FIG. 1 shows siRNA construct targeting LDHa/PDHK1, 2, 3. siRNAs targeting LDHa, PDHK1, PDHK2 and PDHK3 were cloned into single pSilencer 3.1 hygromycin vector. Targeting sequence for LDHa was under U6 promoter regulation whereas siRNAs for PDHK1, 2, and 3 were under H1 promoter regulation.

The present invention provides methods and compositions for reducing lactate production and increasing polypeptide production in cultured cells. The inventors have discovered that concomitant downregulation of a LDH and PDHKs via siRNAs by a process known as RNA interference (RNAi) in cultured cells expressing polypeptides (e.g., antibodies) decreased lactate level, lactate production rate, and cell osmolality, and increased specific polypeptide productivity (e.g., Specific Productivity) and polypeptide production (e.g., productivity). Further, these cultured cells with the downregulated LDH and PDHKs exhibited no negative impact on cell growth, cell viabilities, and the quality of polypeptides produced. Thus, without wishing to be bound by theory, decreasing the pyruvate-lactate conversion by knocking down the expression of a LDH and promoting pyruvate into tricarboxylic acid cycle (TCA or Krebs cycle) by knocking down the expression of one or more PDHKs may create a synergistic effect in lactate reduction and providing cells with more energy and metabolic intermediates. These effects in turn may lead to increased polypeptide (e.g., antibody) production in cultured cells.

Accordingly, in one aspect of the invention, provided is a method for reducing lactate production in cultured cells, comprising culturing cells expressing a) an siRNA specific for a LDH and b) an siRNA specific for a PDHK.

In another aspect, provided are cells in culture comprising a) an si RNA specific for a LDH and an siRNA specific for a PDHK.

In another aspect, the invention provides a method for reducing lactate production in cultured cells, comprising culturing cells comprising a first heterologous nucleic acid sequence encoding an siRNA specific for a LDH and a second heterologous nucleic acid sequence encoding an siRNA specific for a PDHK, wherein the first heterologous nucleic acid sequence is operably linked to a first promoter, and wherein the second heterologous nucleic acid sequence is operably linked to a second promoter.

In yet another aspect, the invention provides cells in culture comprising a first heterologous nucleic acid sequence encoding a first siRNA specific for a LDH and a second heterologous nucleic acid sequence encoding a second siRNA specific for a PDHK, wherein the first heterologous nucleic acid sequence is operably linked to a first promoter, and wherein the second heterologous nucleic acid sequence is operably linked to a second promoter.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

As used herein, the term "cells in culture" or "cultured cells" refers two or more cells in a solution (e.g., a cell medium) that allows the cells to undergo one or more cell divisions.

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, ρ-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "RNA interference (RNAi)" refers to the process of sequence-specific, transcriptional gene silencing (e.g., posttranscriptional gene silencing) mediated or initiated by siRNA. Without wishing to be bound by theory, during RNAi, in practicing the methods of the invention, siRNA can induce degradation of target mRNA with consequent sequence-specific inhibition of gene expression of a LDH and one or more PDHKs.

The term "heterologous nucleic acid" or "heterologous polypeptide" refers to a nucleic acid or a polypeptide whose sequence is not identical to that of another nucleic acid or polypeptide naturally found in the same host cell.

The term "small interfering RNA," "short interfering RNA," or "siRNA" refers to an RNA duplex of nucleotides, or, in some alternative aspects, a single molecule of RNA that is targeted to a nucleic acid of interest, e.g., a LDH or PDHK(s). The siRNA comprise a sense RNA strand and a complementary antisense RNA strand annealed together by standard Watson-Crick base-pairing interactions. SiRNA can either be transfected directly or otherwise produced within a cultured cell.

In one variation, the sense RNA strand and the complementary antisense RNA strand are linked by a spacer leading to the expression of a stem-loop or a hairpin structure termed short hairpin RNA (shRNA). The hairpin is then cleaved by an endonuclease (e.g., Dicer) to generate an siRNA. In another variation, the shRNA is a bi-functional shRNA consisting of two stem-loop structures, with one stem-loop structure composed of fully matched sequence guiding the RNA duplex for mRNA degradation via cleavage dependent RISC(RNA-induced silencing complex) loading, and with the second stem-loop structure composed of mis-matched strand inhibiting translation of the mRNA through mRNA sequestration via cleavage-independent RISC loading.

As used herein, an siRNA "specific" for a LDH or PDHK refers to an siRNA that is targeted to a nucleic acid of interest (e.g., a LDH or PDHK(s)) and that the nucleotide sequence of the duplex portion of the siRNA is complementary to a nucleotide sequence of the targeted gene (e.g., a LDH or PDHK(s)).

As used herein, "operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term "promoter" includes all sequences capable of driving transcription of a coding sequence in a cultured cell, e.g., a mammalian cell. Thus, promoters used in the constructs of the invention include cis-acting transcriptional control elements and regulatory sequences that are involved in regulating or modulating the timing and/or rate of transcription of a gene (e.g., a LDH or PDHK(s)). For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

As used herein, "vector" means a construct, which is capable of delivering, and preferably expressing, one or more gene(s) or sequence(s) of interest (e.g., LDHa and PDHK(s)) in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, $2^{nd}$ ed., Cold Spring Harbor, 1989).

As used herein, the average lactate production rate is calculated as lactate synthesis rate minus lactate consumption rate in mg/cells/day.

As used herein, "Specific Productivity" or "Qp" refers to the specific protein, e.g., antibody, production rate in pg/cell/day. Specific productivity is calculated as protein titer (pg/cell/day)/IVCC (calculate integrated viable cell count; cell/day).

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The term "antibody" is used in the broadest sense and specifically covers monoclonal antibodies (including full length monoclonal antibodies), polyclonal antibodies, multispecific antibodies (e.g., bispecific antibodies), and antibody fragments.

"Antibody fragments" comprise a portion of a full length antibody, generally the antigen binding or variable region thereof. Examples of antibody fragments include Fab, Fab', $F(ab')_2$, and Fv fragments; single-chain antibody molecules; diabodies; linear antibodies; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

As used herein, the term "immunoadhesin" designates antibody-like molecules which combine the "binding domain" of a heterologous "adhesin" protein (e.g. a receptor, ligand or enzyme) with the effector functions of an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains since immunoadhesins comprising these regions can be purified by Protein A chromatography (Lindmark et al., J. Immunol. Meth. 62:1-13 (1983)).

The term "ligand binding domain" as used herein refers to any native cell-surface receptor or any region or derivative thereof retaining at least a qualitative ligand binding of a corresponding native receptor. In a specific embodiment, the receptor is from a cell-surface polypeptide having an extracellular domain which is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule which combines at least one binding domain of an antibody (as herein defined) with at least one immunoadhesin (as defined in this application). Exemplary antibody-immunoadhesin chimeras are the bispecific CD4-IgG chimeras described in Berg et al., PNAS (USA) 88:4723-4727 (1991) and Chamow et al., J. Immunol. 153:4268 (1994).

The term "osmolality" refers to the number of solute particles dissolved in 1 liter of solution. Solutes which can be added to the culture medium so as to increase the osmolality thereof include proteins, peptides, amino acids, non-metabolized polymers, vitamins, ions, salts (e.g., sodium or potassium salts), sugars, metabolites, organic acids, lipids, etc. When used herein, the abbreviation "mOsm" means "milliosmoles/Liter H$_2$O."

As used herein, a "host cell" includes an individual cell, cultured cells, or cell in culture that can be or has been a recipient for vector(s) or siRNA(s) for incorporation of polynucleotide inserts to produce polypeptide. Host cells include progeny of a single cultured cell, and the progeny may not necessarily be completely identical (in morphology or in genomic DNA complement) to the original parent cell due to natural, accidental, or deliberate mutation.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Methods for Reducing Lactate Production

The methods herein involve culturing cells expressing siRNAs specific for a LDH and at least one or more PDHKs to reduce lactate production via RNA interference (RNAi). In one aspect, the method comprises culturing cells expressing a) an siRNA specific for LDH and b) an siRNA specific for a PDHK.

In some embodiments, the cultured cells further express an siRNA specific for a second PDHK. In some embodiments, the cultured cells further express an siRNA specific for a third PDHK. In some embodiments, the cultured cells further express an siRNA specific for a fourth PDHK.

In another aspect, the method comprises a first heterologous nucleic acid sequence encoding an siRNA specific for a LDH and a second heterologous nucleic acid sequence encoding an siRNA specific for a PDHK, wherein the first heterologous nucleic acid sequence is operably linked to a first promoter, and wherein the second heterologous nucleic acid sequence is operably linked to a second promoter.

In another aspect, provided is a method of silencing or down-regulating LDH and PDHK transcription in a cultured cell comprising: introducing into the cell a vector comprising a first heterologous nucleic acid sequence encoding an siRNA specific for the LDH and a second heterologous nucleic acid sequence encoding an siRNA specific for the PDHK, wherein the first heterologous nucleic acid sequence is operably linked to a first promoter, and wherein the second heterologous nucleic acid sequence is operably linked to a second promoter, wherein the siRNAs are expressed, thereby silencing or down-regulating gene transcription of the LDH and the PDHK.

In some embodiments, the cultured cells further comprise a third heterologous nucleic acid sequence encoding an siRNA specific for a second PDHK and wherein the third heterologous nucleic acid sequence is operably linked to a third promoter. In some embodiments, the cultured cells further comprise a fourth heterologous nucleic acid sequence encoding an siRNA specific for a third PDHK and wherein the fourth heterologous nucleic acid sequence is operably linked to a fourth promoter. In some embodiments, the cultured cells further comprise a fifth heterologous nucleic acid sequence encoding an siRNA specific for a fifth PDHK and wherein the fifth heterologous nucleic acid sequence is operably linked to a fifth promoter.

In some embodiments, the LDH is LDHa, LDHb, or LDHc. In some embodiments, the PDHK is selected from the group consisting of PDHK1, PDHK2, PDHK3, and PDHK4. In some embodiments, the PDHK is selected from the group consisting of PDHK1, PDHK2, and PDHK3. In some embodiments, the PDHK is selected from the group consisting of PDHK2, PDHK3, and PDHK4. In some embodiments, the PDHK is selected from the group consisting of PDHK1, PDHK3, and PDHK4. In some embodiments, the PDHK is selected from the group consisting of PDHK1 and PDHK2. In some embodiments, the PDHK is selected from the group consisting of PDHK1 and PDHK3. In some embodiments, the PDHK is selected from the group consisting of PDHK2 and PDHK3. In some embodiments, the PDHK is selected from the group consisting of PDHK2 and PDHK4. In some embodiments, the PDHK is selected from the group consisting of PDHK3 and PDHK4.

In some embodiments, the method comprises culturing cells expressing a) an siRNA specific for LDHa and b) an siRNA specific for PDHK1, PDHK2, and PDHK3, respectively. In some embodiments, the method comprises culturing cells expressing a) an siRNA specific for LDHb and b) an siRNA specific for PDHK1, PDHK2, and PDHK3, respectively. In some embodiments, the method comprises culturing cells expressing a) an siRNA specific for LDHc and b) an siRNA specific for PDHK1, PDHK2, and PDHK3, respectively.

In some embodiments, the method comprises culturing cells expressing a) an siRNA specific for LDHa, LDHb, or LDHc and b) an siRNA specific for two PDHKs, wherein the PDHK is selected from the group consisting of PDHK1, PDHK2, PDHK3, and PDHK4. For example, the method comprises culturing cells expressing a) an siRNA specific for LDHa and b) an siRNA specific for PDHK1 and PDHK2, respectively.

In some embodiments, the mRNA expression level for a LDH is reduced by at least about 75% and the mRNA expression level for a PDHK is reduced by at least about 25% in cultured cells expressing a) an siRNA specific for a LDH and b) an siRNA specific for a PDHK in comparison to cultured cells without the siRNAs specific for a LDH and a PDHK. In some embodiments, the LDH is LDHa, LDHb, or LDHc and the mRNA expression level for the LDH is reduced by at least about 75%, at least about 80%, at least about 85%, at least about 90%, or at least about 95%. In some embodiments, the PDHK is PDHK1, PDHK2, or PDHK3, and the mRNA expression level for the PDHK is reduced by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In some embodiments, in cultured cells expressing a) an siRNA specific for LDHa and b) an siRNA specific for PDHK1, PDHK2, and PDHK3, the mRNA expression level for LDHa is reduced by about 90% and the mRNA expression levels for PDHK1, PDHK2, and PDHK3 are reduced by about 32%, 83%, and 70%, respectively, in comparison to cultured cells without the siRNAs specific for the LDHa, PDHK1, PDHK2, and PDHK3.

In some embodiments, the method comprises a first heterologous nucleic acid sequence encoding an siRNA specific for LDHa, LDHb, or LDHc, a second heterologous nucleic acid sequence encoding an siRNA specific for PDHK1, a third heterologous nucleic acid sequence encoding an siRNA specific for PDHK2, and a fourth heterologous nucleic acid sequence encoding an siRNA specific for PDHK3, wherein the first heterologous nucleic acid sequence is operably linked to a first promoter, and wherein the second, third, and fourth heterologous nucleic acid sequence is operably linked to a second promoter.

In some embodiments, the method comprises a first heterologous nucleic acid sequence encoding an siRNA specific for LDHa, LDHb, or LDHc, a second heterologous nucleic acid sequence encoding an siRNA specific for a PDHK, and a third heterologous nucleic acid sequence encoding an siRNA specific for a PDHK, wherein the first heterologous nucleic acid sequence is operably linked to a first promoter, wherein the second and third heterologous nucleic acid sequences are operably linked to a second promoter, and wherein the PDHK is selected from the group consisting of PDHK1, PDHK2, PDHK3, and PDHK4.

In some embodiments, the mRNA expression level for a LDH is reduced by at least about 75% and the mRNA expression level for a PDHK is reduced by at least about 25% in cultured cells comprising a first heterologous nucleic acid sequence encoding an siRNA specific for a LDH and a second heterologous nucleic acid sequence encoding an siRNA specific for a PDHK in comparison to cultured cells without the heterologous nucleic acid sequence comprising the LDH and the PDHK(s), wherein the first heterologous nuclei acid sequence is operably linked to a first promoter, and wherein the second heterologous nucleic acid sequence is operably linked to a second promoter. In some embodiments, the LDH is LDHa, LDHb, or LDHc and the mRNA expression level for the LDH is reduced by at least about 75%, at least about 80%, at least about 85%, at least about 90%, or at least about 95%. In some embodiments, the PDHK is PDHK1, PDHK2, or PDHK3, and the mRNA expression level for the PDHK is reduced by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In some embodiments, in cultured cells comprising a first heterologous nucleic acid sequence encoding an siRNA specific for LDHa, a second heterologous nucleic acid sequence encoding an siRNA specific for PDHK1, a third heterologous nucleic acid sequence encoding an siRNA specific for PDHK2, and a fourth heterologous nucleic acid sequence encoding an siRNA specific for PDHK3, wherein the first heterologous nucleic acid sequence is operably linked to a first promoter, and wherein the second, third, and fourth heterologous nucleic acid sequence is operably linked to a second promoter, the mRNA expression level for LDHa is reduced by about 90% and the mRNA expression levels for PDHK1, PDHK2, and PDHK3 are reduced by about 32%, 83%, and 70%, respectively, in comparison to cultured cells without the siRNAs specific for the LDHa, PDHK1, PDHK2, and PDHK3.

The siRNA used in the invention described herein can be obtained or made from a variety of sources, e.g., produced in vitro, ex vivo or in vivo, as described herein. In some embodiments, the siRNA can contain from about 1 to about 200 nucleotides, from about 5 to about 100 nucleotides, from about 10 to about 50 nucleotides, from about 15 to about 30 nucleotides, or from about 19 to about 25 nucleotides. In some embodiments, the length of the siRNA is less than 30 nucleotides. In some embodiments, the length of the siRNAs is more than 30 nucleotides. In some embodiments, the siRNA can be 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9 or less nucleotides in length.

In some embodiments, the siRNA can be generated by chemical synthesis, by in vitro transcription using a polymerase, or by an endoribonuclease (e.g., Dicer) digestion of long double strand RNA (dsRNA). In some embodiments, the siRNA can be entirely, or in part, comprised of synthetic nucleotides, natural bases or modified bases.

In some embodiments, the siRNA can be expressed intracellularly. The siRNA can be encoded by a nucleic acid sequence, and the nucleic acid sequence can also include one or more promoters. The nucleic acid sequence can also include a polyadenylation signal. In some embodiments, sense and antisense strands of the RNA duplex can be produced from two independent promoters and annealed with the cultured cell. In some embodiments, the sense and antisense strands of the RNA duplex can also be linked by a base pair spacer (e.g., a base pair spacer may comprise a single or multiple base pair) or a stem-loop to form a shRNA and expressed by a single promoter. In some embodiments, the shRNA can be a bi-functional shRNA. The hairpin can be cleaved by an endoribonuclease (e.g., Dicer) to generate effective siRNA molecules. The spacer or stem-loop is positioned between the sense and antisense strands that form the duplex. The stem-loop can vary in length. In some embodiments, the stem-loop is 2, 3, 4, 5, 6, 7, 8, 9, 10, 11, 12, 13, 14, or 15 or more nucleotides in length. The hairpin structure can also contain 3' or 5' overhang portions. In some embodiments, the overhang is a 3' or a 5' overhang 1, 2, 3, 4 or 5 nucleotides in length. Compositions and methods for RNA-mediated gene regulation by siRNA, shRNA, or bifunctional shRNA are described, for example, in U.S. Appl. No. 20090215860, Rutz and Scheffold, *Arthritis Research & Therapy*, 6(2):78-85 (2004), and Rao et al., *Advanced Drug Delivery Reviews* 61:746-759 (2009).

In some embodiments, the siRNA used in the present invention can have perfect homology with target sequences to produce target specific responses. In some embodiments, the siRNA used in the present invention have about any of 99%, 98%, 97%, 96%, 95%, 94%, 92%, 91%, 90%, 88%, 86%, 84%, 82%, 80%, 78%, 76%, 74%, 72%, 70%, 65%, 60%, 55%, 50%, 45%, 40%, 35%, 30%, 25%, 20%, 15%, 10%, or 5%, homology with target sequences. In one variation, the siRNA used in the present invention can hybridize under physiologic conditions to a nucleic acid target sequence, e.g., it can specifically hybridize to a target sequence in a cell, e.g., in vivo. In another variation, the siRNA targets more than one target sequence, target marker or reporter gene.

The extent of sequence identity (homology) necessary for in vivo targeting of an siRNA to a target nucleic acid (e.g., specific binding of an siRNA to a target sequence in a cell under physiologic conditions) can be tested under routine screening conditions, e.g., in cell culture and the like.

In some embodiments, the target sequence for PDHK1 is GCAGTTCCTGGACTTCGGA (SEQ ID NO:2). In some embodiments, the target sequence for PDHK2 is CATTCAGTACTTCTTGGAC (SEQ ID NO:3). In some embodiments, the target sequence for PDHK3 is TGTAGCTGATGTCGTGAAA (SEQ ID NO:4).

Lactate dehydrogenase (LDH) converts pyruvate into lactate. The accession numbers of exemplary LDH (e.g., LDHa, LDHb, or LDHc) polypeptides and nucleic acids include, but are not limited to, DQ912661 (LDHa in CHO cells), BC067223 (human LDHa), BC084698 (rat LDHa), BC094428 (mouse LDHa), BC002362 (human LDHb), NM_012595 (rat LDHb), NM_008492 (mouse LDHb), BC090043 (human LDHc), NM_017266 (rat LDHc), and NM_013580 (mouse LDHc). Standard methods known by persons skill in the art can be used to determine whether a LDH polypeptide has LDH activity by measuring the ability of the polypeptide to convert pyruvate into lactate in vitro, in a cell extract, or in vivo.

Pryuvate dehydrogense kinase (PDHK) inhibits the conversion of pyruvate into acetyl-CoA. The accession numbers of exemplary PDHK1 polypeptides and nucleic acids include, but are not limited to, L42450 (human), BC089783 (rat), and NM_172665 (mouse). The accession numbers of exemplary PDHK2 polypeptides and nucleic acids include, but are not limited to, NM_002611 (human), NM_030872 (rat), and NM_133667 (mouse). The accession numbers of exemplary PDHK3 polypeptides and nucleic acids include, but are not limited to, L42452 (human), BC169078 (rat), and NM_145630 (mouse). The accession numbers of exemplary PDHK4 polypeptides and nucleic acids include, but are not limited to, NM_002612 (human), NM_053551 (rat), and NM_013743 (mouse). Standard methods known by person skilled in the art can be used to determine whether a PDHK polypeptide has PDHK activity by measuring the ability of the polypeptide to inhibit the conversion of pyruvate into acetyl-CoA in vitro, in a cell extract, or in vivo.

Promoters are well known in the art. Any promoter that functions in the host cell can be used for expression of siRNAs specific for a LDH and one or more of PDHK in the host cell. Virtually any promoter capable of driving these siRNAs is suitable for the present invention including, but not limited to, U6, H1, CYC1, HIS3, GAL1, GAL4, GAL10, ADH1, PGK, PHO5, GAPDH, T7, CMV, SV40, and EF1a. For example, in some embodiments, the method comprises a first heterologous nucleic acid sequence encoding an siRNA specific for LDHa, a second heterologous nucleic acid sequence encoding an siRNA specific for PDHK1, a third heterologous nucleic acid sequence encoding an siRNA specific for PDHK2, and a fourth heterologous nucleic acid sequence encoding an siRNA specific for PDHK3, wherein the first heterologous nucleic acid sequence is operably linked to a first promoter U6, and wherein the second, third, and fourth heterologous nucleic acid sequences are operably linked to a second promoter H1. In one variation, the first heterologous nucleic acid sequence encoding an siRNA is specific for LDHb. In another variation, the first heterologous nucleic acid sequence encoding an siRNA is specific for LDHc.

In another aspect, provided is a method of making a cell that exhibits decreased lactate production in culture, comprising introducing into the cell a vector comprising a first heterologous nucleic acid sequence encoding an siRNA specific for the LDH and a second heterologous nucleic acid sequence encoding an siRNA specific for the PDHK, wherein the first heterologous nucleic acid sequence is operably linked to a first promoter, and wherein the second heterologous nucleic acid sequence is operably linked to a second promoter.

The first heterologous nucleic acid sequence encoding an siRNA specific for the LDH and the second heterologous nucleic acid sequence encoding the siRNA specific for the PDHK can be inserted into a vector by a variety of procedures. For example, the LDH and PDHK siRNA sequences are ligated to the desired position in the vector following digestion of the insert and the vector with appropriate restriction endonucleases, such as KasI, BamHI, HindIII, or BhIII. In some embodiments, a vector containing siRNAs sequences specific for LDHa and PDHK1, PDHK2, and PDHK3 are constructed by inserting the LDHa siRNA sequence into the KasI site of the vector (e.g., pSilencer 3.1-H1 hygro vector) with an addition of U6 promoter at its immediate 5' end, inserting the PDHK1 and PDHK2 siRNA sequences into BamHI/HindIII and HindIII sites, respectively, and inserting the PDHK3 siRNA sequence into BgIII with an addition of H1 promoter at the immediate 5' ends of PDHK1, PDHK2, and PDHK3. Cultured cells expressing decreased lactate production can then be generated by transfecting the vectors containing LDHa and PDHK1, PDHK2, and PDHK3 siRNA.

Compositions

The cultured cells produced by the methods described herein are also provided in the present invention. The compositions of the present invention can be practiced in vivo, ex vivo, or in vitro. In one aspect, provided are cells in culture expressing a) an siRNA specific for LDH and b) an siRNA specific for a PDHK. In some embodiments, the cultured cells further express an siRNA specific for a second PDHK. In some embodiments, the cultured cells further express an siRNA specific for a third PDHK. In some embodiments, the cultured cells further express an siRNA specific for a fourth PDHK.

In some embodiments, cells in culture express a) an siRNA specific for LDHa and b) an siRNA specific for PDHK1, PDHK2, and PDHK3, respectively. In some embodiments, cells in culture express a) an siRNA specific for LDHb and b) an siRNA specific for PDHK1, PDHK2, and PDHK3, respectively. In some embodiments, cells in culture express a) an siRNA specific for LDHc and b) an siRNA specific for PDHK1, PDHK2, and PDHK3, respectively.

In some embodiments, cells in culture express a) an siRNA specific for LDHa and b) an siRNA specific for two PDHKs, wherein the PDHK is selected from the group consisting of PDHK1, PDHK2, PDHK3, and PDHK4. In some embodiments, cells in culture express a) an siRNA specific for LDHb and b) an siRNA specific for two PDHKs, wherein the PDHK is selected from the group consisting of PDHK1, PDHK2, PDHK3, and PDHK4. In some embodiments, cells in culture express a) an siRNA specific for LDHc and b) an siRNA specific for two PDHKs, wherein the PDHK is selected from the group consisting of PDHK1, PDHK2, PDHK3, and PDHK4.

In another aspect, provided are cells in culture comprising a first heterologous nucleic acid sequence encoding an siRNA specific for a LDH and a second heterologous nucleic acid sequence encoding an siRNA specific for a PDHK, wherein the first heterologous nucleic acid sequence is operably linked to a first promoter, and wherein the second heterologous nucleic acid sequence is operably linked to a second promoter. In some embodiments, the cells further comprise a third heterologous nucleic acid sequence encoding an siRNA specific for a second PDHK and wherein the third heterologous nucleic acid sequence is operably linked to a third promoter. In some embodiments, the cells further comprise a fourth heterologous nucleic acid sequence encoding an siRNA specific for a third PDHK and wherein the fourth heterologous nucleic acid sequence is operably linked to a fourth promoter. In some embodiments, the cells further comprise a fifth heterologous nucleic acid sequence encoding an siRNA specific for a fifth PDHK and wherein the fifth heterologous nucleic acid sequence is operably linked to a fifth promoter.

In some embodiments, cells in culture comprises a first heterologous nucleic acid sequence encoding an siRNA specific for LDHa, a second heterologous nucleic acid sequence encoding an siRNA specific for PDHK1, a third heterologous nucleic acid sequence encoding an siRNA specific for PDHK2, and a fourth heterologous nucleic acid sequence encoding an siRNA specific for PDHK3, wherein the first heterologous nucleic acid sequence is operably linked to a first promoter (e.g., U6), and wherein the second, third, and fourth heterologous nucleic acid sequences are operably linked to a second promoter (e.g., H1). In one variation, the first heterologous nucleic acid sequence encoding an siRNA is specific for LDHb. In another variation, the first heterologous nucleic acid sequence encoding an siRNA is specific for LDHb.

In some embodiments, cells in culture comprise a first heterologous nucleic acid sequence encoding an siRNA specific for LDHa, a second heterologous nucleic acid sequence encoding an siRNA specific for a PDHK, a third heterologous nucleic acid sequence encoding an siRNA specific for a PDHK, wherein the PDHK is selected from the group consisting of PDHK1, PDHK2, PDHK3, and PDHK4, wherein the first heterologous nucleic acid sequence is operably linked to a first promoter (e.g., U6), and wherein the second and the third heterologous nucleic acid sequences are operably linked to a second promoter (e.g., H1). In one variation, the first heterologous nucleic acid sequence encoding an siRNA is specific for LDHb. In another variation, the first heterologous nucleic acid sequence encoding an siRNA is specific for LDHc.

In some embodiments, the cell culture includes at least about 5, 10, 15, 20, 50, 75, 100, 200, 500, 750, 1,000, 5,000, 7,500, 10,000, 15,000 or more cells.

In another aspect, provided are cells in culture having a lactate synthesis rate that is lower than a lactate consumption rate. In some embodiments, the cells in culture have an average lactate production rate of less than about any of negative 0.2 mg/$10^6$ cells/day, negative 0.1 mg/$10^6$ cells/day, negative 0.08 mg/$10^6$ cells/day, negative 0.06 mg/$10^6$ cells/day, negative 0.04 mg/$10^6$ cells/day, negative 0.02 mg/$10^6$ cells/day, negative 0.01 mg/$10^6$ cells/day, negative 0.008 mg/$10^6$ cells/day, negative 0.006 mg/$10^6$ cells/day, negative 0.004 mg/$10^6$ cells/day, or negative 0.002 mg/$10^6$ cells/day.

In some embodiments, cells in culture comprises a first heterologous nucleic acid sequence encoding an siRNA specific for LDHa, a second heterologous nucleic acid sequence encoding an siRNA specific for PDHK1, a third heterologous nucleic acid sequence encoding an siRNA specific for PDHK2, and a fourth heterologous nucleic acid sequence encoding an siRNA specific for PDHK3, wherein the first heterologous nucleic acid sequence is operably linked to a first promoter (e.g., U6), wherein the second, third, and fourth heterologous nucleic acid sequences are operably linked to a second promoter (e.g., H1), and wherein the cells in culture have an average lactate production rate of about negative 0.02 mg/$10^6$ cells/day.

In another aspect, provided are cells in culture containing siRNA specific for a LDH and PDHK(s) having a decreased osmolality. In some embodiments, cells in culture containing siRNA specific for a LDH and PDHK(s) have an osmolality at less than about any of 500 mOsm, 450 mOsm, 400 mOsm, 350 mOsm, 300 mOsm, 250 mOsm, 200 mOsm, or 150 mOsm.

In some embodiments, cells in culture comprises a first heterologous nucleic acid sequence encoding an siRNA specific for LDHa, a second heterologous nucleic acid sequence encoding an siRNA specific for PDHK1, a third heterologous nucleic acid sequence encoding an siRNA specific for PDHK2, and a fourth heterologous nucleic acid sequence encoding an siRNA specific for PDHK3, wherein the first heterologous nucleic acid sequence is operably linked to a first promoter (e.g., U6), wherein the second, third, and fourth heterologous nucleic acid sequence is operably linked to a second promoter (e.g., H1, and wherein the cells in culture have an osmolality at about 300 mOsm.

In another aspect, provided are cells in culture having an increased Specific Productivity (Qp). In some embodiments, the cultured cells have a Specific Productivity of at least about 60% higher, at least about 65% higher, at least about 70% higher, at least about 75% higher, at least about 80% higher, at least about 85% higher, at least about 90% higher, or at least about 95% higher than cultured cells without the heterologous nucleic acid sequence comprising the PDHK(s) and the LDH. In some embodiments, the cultured cells have a Specific Productivity of about 67% higher, about 69% higher, about 71% higher, about 72% higher, about 73% higher, about 74% higher, about 75% higher, about 76% higher, about 77% higher, about 78% higher, about 79% higher, about 81% higher, about 83% higher, about 85% higher, about 87% higher, about 89% higher, about 91% higher, about 93% higher, about 95% higher, about 97% higher, or at about 99% higher than cultured cells without the heterologous nucleic acid sequence comprising the PDHK(s) and the LDH.

In some embodiments, cells in culture comprises a first heterologous nucleic acid sequence encoding an siRNA specific for LDHa, a second heterologous nucleic acid sequence encoding an siRNA specific for PDHK1, a third heterologous nucleic acid sequence encoding an siRNA specific for PDHK2, and a fourth heterologous nucleic acid sequence encoding an siRNA specific for PDHK3, wherein the first heterologous nucleic acid sequence is operably linked to a first promoter (e.g., U6), wherein the second, third, and fourth heterologous nucleic acid sequence is operably linked to a second promoter (e.g., H1), and wherein the cells in culture have a Specific Productivity of about 75% higher.

In another aspect, provided are the cultured cells produced by the method herein with an increased polypeptide productivity (e.g., antibody productivity or titer in g/L). In some embodiments, the cultured cells have a polypeptide productivity of about 10% to about 800% higher than cultured cells without the heterologous nucleic acid sequence comprising the PDHK(s) and the LDH. In some embodiments, the cultured cells have a polypeptide productivity of about 10% higher, about 15% higher, about 20% higher, about 25% higher, about 30% higher, about 35% higher, about 40% higher, about 45% higher, about 50% higher, about 55% higher, about 58% higher, about 60% higher, about 65% higher, about 70% higher, about 71% higher, about 75% higher, about 80% higher, about 85% higher, about 90% higher, about 95% higher, about 100% higher, about 125% higher, about 150%, about 200% higher, about 250% higher, about 300% higher, about 350% higher, about 400% higher, about 450% higher, about 500 higher, about 550% higher, about 600% higher, about 650% higher, about 700% higher, about 750% higher, or about 800% higher than cultured cells without the heterologous nucleic acid sequence comprising the PDHK(s) and the LDH. In some embodiments, the cultured cells have a polypeptide productivity of at least about 55% higher, at least about 60% higher, at least about 65% higher, at least about 68% higher, at least about 70% higher, at least about 80% higher, at least about 85% higher, or at least about 90% higher than cultured cells without the heterologous nucleic acid sequence comprising the PDHK(s) and the LDH.

In some embodiments, cells in culture comprises a first heterologous nucleic acid sequence encoding an siRNA specific for LDHa, a second heterologous nucleic acid sequence encoding an siRNA specific for PDHK1, a third heterologous nucleic acid sequence encoding an siRNA specific for PDHK2, and a fourth heterologous nucleic acid sequence encoding an siRNA specific for PDHK3, wherein the first heterologous nucleic acid sequence is operably linked to a first promoter (e.g., U6), wherein the second, third, and fourth heterologous nucleic acid sequence is operably linked to a second promoter (e.g., H1), and wherein the cultured cells have an antibody productivity (e.g., in g/L) of at least about 68% higher than cultured cells without the heterologous nucleic acid sequence comprising the PDHK1, PDHK2, PDHK3, and LDHa.

In some embodiments, the cultured cells have a polypeptide productivity of about 10% to about 800% higher than cultured cells without the siRNAs specific for the PDHK(s) and the LDH (in some embodiments, an antibody). In some embodiments, the cultured cells have a polypeptide productivity of about 10% higher, about 15% higher, about 20% higher, about 25% higher, about 30% higher, about 35% higher, about 40% higher, about 45% higher, about 50% higher, about 55% higher, about 60% higher, about 65% higher, about 70% higher, about 75% higher, about 80% higher, about 85% higher, about 90% higher, about 95% higher, about 100% higher, about 125% higher, about 150%, about 200% higher, about 250% higher, about 300% higher, about 350% higher, about 400% higher, about 450% higher, about 500 higher, about 550% higher, about 600% higher, about 650% higher, about 700% higher, about 750% higher, or about 800% higher than cultured cells without the siRNAs specific for the PDHK(s) and the LDH. In some embodiments, the cultured cells have a polypeptide productivity of at least about 65% higher, at least about 68% higher, at least about 70% higher, at least about 80% higher, at least about 85% higher, or at least about 90% higher than cultured cells w without the siRNAs specific for the PDHK(s) and the LDH. In some embodiments, the antibody productivity is at least about 68% higher than cultured cells without the siRNAs specific for the PDHK(s) and the LDH.

In another aspect, provided is a vector comprising a first heterologous nucleic acid sequence encoding an siRNA specific for a LDH and a second heterologous nucleic acid sequence encoding an siRNA specific for a PDHK, wherein the first heterologous nucleic acid sequence is operably linked to a first promoter, and wherein the second heterologous nucleic acid sequence is operably linked to a second promoter.

In some embodiments, the vector contains a nucleic acid under the control of an expression control sequence. As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector also includes a termination sequence. Termination control regions may also be derived from various genes native to the host cell. In some embodiments, the termination sequence and the promoter sequence are derived from the same source. In another embodiment, the termination sequence is endogenous to the host cell. Optionally, a termination site may be included. For effective expression of the polypeptides, DNA encoding the polypeptide are linked operably through initiation codons to selected expression control regions such that expression results in the formation of the appropriate messenger RNA.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some embodiments, the selective marker is the hygromycin nucleic acid.

Polypeptides

The polypeptide or protein to be produced using the methods and cultured cells described herein includes, but is not limited to, antibody or immunoadhesin. Techniques for generating such molecules are discussed below.

Antibodies

Antibodies within the scope of the present invention include, but are not limited to: anti-CD20 antibodies such as chimeric anti-CD20 "C2B8" as in U.S. Pat. No. 5,736,137 (RITUXAN®); anti-VEGF antibodies, including humanized and/or affinity matured anti-VEGF antibodies such as the humanized anti-VEGF antibody huA4.6.1 AVASTIN® (Kim et al., *Growth Factors*, 7:53-64 (1992), International Publication No. WO 96/30046, and WO 98/45331, published Oct. 15, 1998) and V3LA; anti-MUC16 antibody; anti-CD4 antibodies such as the cM-7412 antibody (Choy et al. *Arthritis Rheum.* 39(1):52-56 (1996)) and the Ibalizumab (TNX355) antibody; anti-MET antibodies such as one-armed 5D5 anti-C-Met antibody; anti-HER2 antibodies Trastuzumab (HERCEPTIN®) (Carter et al., *Proc. Natl. Acad. Sci. USA,* 89:4285-4289 (1992), U.S. Pat. No. 5,725,856) and humanized 2C4 (WO01/00245, Adams et al.), a chimeric or humanized variant of the 2H7 antibody as in U.S. Pat. No. 5,721,108B1, or Tositumomab (BEXXAR®); anti-IL-8 antibodies (St John et al., *Chest,* 103:932 (1993), and International Publication No. WO 95/23865); anti-prostate stem cell antigen (PSCA) antibodies (WO01/40309); anti-CD40 antibodies, including S2C6 and humanized variants thereof (WO00/75348); anti-CD1 antibodies (U.S. Pat. No. 5,622,700, WO 98/23761, Steppe et al., *Transplant Intl.* 4:3-7 (1991), and Hourmant et al., *Transplantation* 58:377-380 (1994)); anti-CD18 (U.S. Pat. No. 5,622,700, issued Apr. 22, 1997, or as in WO 97/26912, published Jul. 31, 1997); anti-IgE antibodies (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338, Presta et al., *J. Immunol.* 151:2623-2632 (1993), and International Publication No. WO 95/19181); anti-Apo-2 receptor antibodies (WO 98/51793 published Nov. 19, 1998); anti-TNF-α antibodies, including cA2 (REMICADE®), CDP571 and MAK-195 (See, U.S. Pat. No. 5,672,347 issued Sep. 30, 1997, Lorenz et al. *J. Immunol.* 156(4):1646-1653 (1996), and Dhainaut et al. *Crit. Care Med.* 23(9):1461-1469 (1995)); anti-Tissue Factor (TF) antibodies (European Patent No. 0 420 937 B1 granted Nov. 9, 1994); anti-human α4β7 integrin antibodies (WO 98/06248 published Feb. 19, 1998); anti-epidermal growth factor receptor (EGFR) antibodies (e.g. chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-Tac antibodies such as CHI-621 (SIMULECT® and ZENAPAX® (See U.S. Pat. No. 5,693,762 issued Dec. 2, 1997); anti-CD52 antibodies such as CAMPATH-1H (Riechmann et al. *Nature* 332:323-337 (1988)); anti-Fc receptor antibodies such as the M22 antibody directed against FcγRI as in Graziano et al. *J. Immunol.* 155(10):4996-5002 (1995); anti-carcinoembryonic antigen (CEA) antibodies such as hMN-1 4 (Sharkey et al. *Cancer Res.* 55(23Suppl): 5935s-5945s (1995); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J Immunol.* 26(1): 1-9 (1996)); anti-CD38 antibodies, e.g. AT 13/5 (Ellis et al. *J. Immunol.* 155(2):925-937 (1995)); anti-CD33 antibodies such as Hu M195 (Jurcic et al. *Cancer Res* 55(23 Suppl):5908s-5910s (1995) and CMA-676 or CDP771; anti-CD22 antibodies such as LL2 or LymphoCide (Juweid et al. *Cancer Res* 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibodies, such as OvaRex; anti-idiotypic GD3 epitope antibody BEC2; anti-αvβ3 antibodies, including VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1).

Aside from the antibodies specifically identified above, the skilled practitioner can generate antibodies directed against an antigen of interest, e.g., using the techniques described below.

(i) Antigen Selection and Preparation

The antibody herein is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22 and CD34; members of the ErbB receptor family such as the EGFR, HER$^2$, HER$^3$ or HER$^4$ receptor; cell adhesion molecules such as LFA-1, Mac1, p1 50,95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to {fraction (1/10)} the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al, *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Protein A-Sepharose, hydroxylapatite chromatography, gel electrophoresis, dialysis, or affinity chromatography. Preferably the Protein A affinity chromatography procedure using a pH gradient described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Monoclonal antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional hybridoma techniques for isolation of monoclonal antibodies.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.,* 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al. *Nature* 355:258 (1992). Human antibodies can also be derived from phage-display libraries (Hoogenboom et al., *J. Mol. Biol.,* 227:381 (1991); Marks et al., *J. Mol. Biol.,* 222:581-597 (1991); Vaughan et al. *Nature Biotech* 14:309 (1996)).

(v) Antibody Fragments

Various techniques have been developed for the production of antibody fragments. Traditionally, these fragments were derived via proteolytic digestion of intact antibodies (see, e.g., Morimoto et al. *Journal of Biochemical and Biophysical Methods* 24:107-117 (1992) and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. A single chain Fv fragment (scFv) can also be isolated. See WO 93/16185. Other techniques for the production of antibody fragments will be apparent to the skilled practitioner.

(vi) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytic ally cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J. Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994). Alternatively, the antibodies can be "linear antibodies" as described in Zapata et al. *Protein Eng.* 8(10):1057-1062 (1995). Briefly, these antibodies comprise a pair of tandem Fd segments ($V_H$-$C_H$1-$V_H$ and $V_L$) which form a pair of antigen binding regions. Linear antibodies can be bispecific or monospecific.

Antibodies with more than two valencies are contemplated. For example, trispecific antibodies can be prepared. Tutt et al. *J. Immunol.* 147: 60 (1991).

Immunoadhesins

The simplest and most straightforward immunoadhesin design combines the binding domain(s) of the adhesin (e.g., the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In some embodiments, the adhesin sequence is fused to the N-terminus of the Fc domain of immunoglobulin $G_1$ (Ig $G_1$). It is possible to fuse the entire heavy chain constant region to the adhesin sequence. However, preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In some embodiments, the adhesin amino acid sequence is fused to (a) the hinge region and or $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagramed below:

(a) $AC_L$-$AC_L$;
(b) $AC_H$-($AC_H$, $AC_L$-$AC_H$, $AC_L$-$V_HC_H$, or $V_LC_L$-$AC_H$);
(c) $AC_L$-$AC_H$-($AC_L$-$AC_H$, $AC_L$-$V_HC_H$, $V_LC_L$-$AC_H$, or $V_LC_L$-$V_HC_H$)
(d) $AC_L$-$V_HC_H$-($AC_H$, or $AC_L$-$V_HC_H$, or $V_LC_L$-$AC_H$);
(e) $V_LC_L$-$AC_H$-($AC_L$-$V_HC_H$, or $V_LC_L$-$AC_H$); and
(f) $(A-Y)_n$-$(V_LC_L$-$V_HC_H)_2$, wherein each A represents identical or different adhesin amino acid sequences;
$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g., Aruffo et al., *Cell* 61:1303-1313 (1990); and Stamenkovic et al., *Cell* 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

Expression of Polypeptides

The polypeptide (e.g., antibody) to be produced using the method described herein is generally produced using recombinant techniques.

Suitable host cells for cloning or expressing the siRNAs in the vectors herein are the prokaryote, yeast, or higher eukaryotic cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable cultured cells for the expression of glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian cell lines include, but are not limited to, monkey kidney CV1 cells transformed by SV40 (COS-7, ATCC CRL 1651); human embryonic kidney cells (293 or 293 cells subcloned for growth in suspension culture, Graham et al., *J. Gen Virol.* 36:59 (1977)); baby hamster kidney cells (BHK, ATCC CCL 10); Chinese hamster ovary cells/DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and human hepatoma cells (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

The host cells used to produce the polypeptide used in the methods of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), (Sigma), or GIBCO® Dulbecco's Modified Eagle Medium: Nutrient Mixture F-12 (Invitrogen) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Other defined or synthetic growth media may also be used, and the appropriate medium for growing a specific type of host cells are known by one of skill in the art of molecular and cell biology. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMY-CIN™, hygromycin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Standard cell culture conditions can be used to culture the cells. Cells are grown and maintained at an appropriate temperature, gas mixture, and pH (such as at about 20° C. to about 37° C., at about 6% to about 84% $CO_2$, and at a pH between about 5 to about 9). In some embodiments, cells are grown in an appropriate cell medium at 37° C. for the first 48 hours, and shifted to 33° for the next 12 days. Reactions may be performed under aerobic or anoxic conditions based on the requirements of the host cells. In some embodiments, the cells are grown using any known mode of fermentation, including, but not limited to, batch, fed-batch, or continuous processes.

When using recombinant techniques, the polypeptide can be produced intracellularly, in the periplasmic space, or directly secreted into the medium. If the polypeptide is produced intracellularly, as a first step, the particulate debris, either host cells or lysed cells (e.g. resulting from homogenization), is removed, for example, by centrifugation or ultrafiltration. Where the polypeptide is secreted into the medium, supernatants from such expression systems are generally first concentrated using a commercially available protein concentration filter, for example, an Amicon or Millipore Pellicon ultrafiltration unit.

Kits

The present invention also provides kits comprising compositions and instructions for use comprising description of the methods of the invention. The kits can comprise cultured cells, siRNAs, target sequences, transfecting agents, instructions for the methods of the present invention, or any combination thereof.

The following examples are provided to illustrate, but not to limit, the invention.

EXAMPLES

It is understood that the examples and embodiments described herein are for illustrative purposes only and that various modifications or changes in light thereof will be suggested to persons skilled in the art and are to be included within the spirit and purview of this application.

Example 1

Knocking Down of PDHK1, PDHK2, PDHK3, and LDHa Reduces Lactate Production and Increases Antibody Titer/Productivity Materials and Methods
Construction of the Vector Targeting LDHa/PDHK1, 2, 3

Targeting sequence for LDHa was selected as described previously by Kim and Lee et al, *Appl. Microbiol. Biotechnol.* 74(1):152-159 (2007), and the LDHa siRNA sequence is CTCGATTCCGTTATCTGAT (SEQ ID NO:1). To design the siRNA-targeted sequence for PDHKs, partial cDNA sequences for CHO PDHK1, 2, and 3 were cloned by reverse transcription of polymerase chain reaction (RT-PCR) with primers located within the highly conserved regions of PDHKs. Partially cloned sequences were used for siRNA sequence designing according to the method described by Elbashier et al. (*Methods* 26:199-213 (2002)).

```
PDHK1 targeting (siRNA) sequence:
                                  (SEQ ID NO: 2)
GCAGTTCCTGGACTTCGGA PDHK2 targeting (siRNA) sequence:
                                  (SEQ ID NO: 3)
CATTCAGTACTTCTTGGAC PDHK3 targeting (siRNA) sequence:
                                  (SEQ ID NO: 4)
TGTAGCTGATGTCGTGAAA
```

The single construct containing targeting sequences for LDHa and PDHKs was constructed using the pSilencer 3.1-H1 hygro vector (Cat#. AM5766, Applied Biosystems/Ambion, Austin, Tex.). LDHa siRNA was inserted into the KasI site of pSilencer 3.1, with an addition of U6 promoter from pSilencer 2.1 at its immediate 5' end. SiRNA sequences for PDHK1 and 2 siRNAs were inserted into BamHI/HindIII and HindIII sites respectively. A BgIII site was introduced to the 3' side of PDHK2 siRNA and used for the insertion of PDHK3 siRNA. For negative control, pSilencer 3.1 vector containing a scrambled siRNA sequence was utilized.

Cell Culture

CHO cells deficient in dihydrofolate reductase (DHFR) were cultured in a proprietary DMEM/F12-based medium in shake flask vessels at 37° C. and 5% $CO_2$. Cells were passaged every three to four days.

Stable siRNA Cell Line (siRNA Clone) Development

A CHO cell line resistant to 25 nM methotrexate (MTX) and expressing a recombinant monoclonal antibody was transfected using Lipofectamine 2000 CD (Cat#12566-014, Invitrogen, Carlsbad, Calif.) according to manufacturer's recommendation (Invitrogen, Carlsbad, Calif.). Transfected cells were centrifuged and seeded into DMEM/F-12-based selective (glycine-, hypoxanthine- and thymidine-free) medium containing 25 nM MTX and 400 ug/ml hygromycin (Cat #10687010, Invitrogen, Carlsbad, Calif.). Re-suspended cells were plated into 96-well plates to generate individual clones. SiRNA clones were derived from siRNA plasmid transfection containing targeting sequences for LDHa and PDHKs genes, while mock clones were derived from mock plasmid (Cat#AM5766, Applied Biosystems/Ambion, Austin, Tex.) transfection containing a scramble sequence designed by manufacture with no appreciable homology to known genes.

Quantitative Real Time PCR (qRT-PCR or Taqman) Analysis

Total RNA from individual clones were isolated using the RNeasy 96 kit (Cat#74181, Qiagen) and were treated with DNase digestion (Cat#79254, RNase free DNase set, Qiagen) to remove residual DNA possibly present in isolated RNA samples. Taqman was performed using universal qRT-PCR master mix according to the manufacturer's instructions (Cat#4309169, Applied Biosystems) and expression levels of PDHKs and LDHa were normalized to housekeeping gene β-microglobulin.

The primers and probe sequences used for Taqman analysis were as follows:

```
PDHK1 forward primer:
                                          (SEQ ID NO: 5)
GCCCATCTCATCGAAAACA PDHK1 reverse primer:
                                          (SEQ ID NO: 6)
AGCCATCTTTAATGACTTCGACTAC PDHK1 probe:
                                          (SEQ ID NO: 7)
TCGCAGTTTGGATTTATGCTTCCAATG PDHK2 forward primer:
                                          (SEQ ID NO: 8)
GATCTGTCCATCAAAATGAGTGA PDHK2 reverse primer:
                                          (SEQ ID NO: 9)
TGTGGAGTACATGTAGCTGAAGAG PDHK2 probe:
                                          (SEQ ID NO: 10)
CTCTCAATCTTCCTCAAGGGGACACC PDHK3 forward primer:
                                          (SEQ ID NO: 11)
CAGCCTGGAGCCTACAAGA PDHK3 reverse primer:
                                          (SEQ ID NO: 12)
GGCATACAGTCGAGAAATTGG PDHK3 probe:
                                          (SEQ ID NO: 13)
AAGCCATAACCAAATCCAGCCAAGG LDHa forward primer:
                                          (SEQ ID NO: 14)
GCCGAGAGCATAATGAAGAA LDHa reverse primer:
                                          (SEQ ID NO: 15)
CCATAGAGACCCTTAATCATGGTA LDHa probe:
                                          (SEQ ID NO: 16)
CTTAGGCGGGTGCATCCCATTT β-microglobulin forward primer:
                                          (SEQ ID NO: 17)
TCCTCTCAGTGGTCT GCT TGG β-microglobulin reverse primer:
                                          (SEQ ID NO: 18)
TGGCGTGTGTAGACTTGCACTT β-microglobulin probe:
                                          (SEQ ID NO: 19)
TGCCATCCAGCGTCCCCCA
```

Fed-Batch Shake Flask Clone Evaluation

Twelve siRNA clones and twelve mock clones were seeded into the proprietary production medium with a pH of 7.15 employing a 14-day fed-batch culture process with one bolus feed on day 3 and a temperature shift from 37° C. to 33° C. on day 2. Cell viability and viable cell counts were monitored by Trypan blue dye exclusion using a Vicell (Beckman Coulter). Lactate concentrations were measured on day 3, 7, 10 and 14 using a Nova Bioprofile analyzer (Nova biomedical). The average cell specific lactate production rate, $q_S$ is calculated as the slope of the graph of integrated total cell number, and the cumulative lactate produced, $[S_t-S_0]$, based on the lactate mass balance equation formulated over the whole culture volume:

$$S_t - S_0 = q_s \int_0^t X dt$$

where $S_t$ is the total amount of lactate in the culture volume (mg) at time t, $S_0$ is the total amount of lactate in the culture volume (mg) at time t=0, X is the total number of cells in the culture volume at any given time 4 and $q_S$ is the specific lactate production rate in mg/cell/day. Since the above equation is written for the time interval between t=0 and t=t, $q_S$ is the average lactate production rate over this time interval. Per the convention used in this work, if more lactate is produced than consumed by the cell, then the value of $q_S$ is positive.

Bioreactor Fed-Batch Operation

Bioreactor experiments were performed in 2 L stirred tank bioreactors (Applikon, Foster City, Calif.) operated at 1.5 L working volume. After a concentrated nutrient feed at 72 hours post-inoculation, glucose was added as needed during the 14-day fed-batch culture. Dissolved oxygen and agitation were maintained in the bioreactor cultures at setpoints of 30% of air saturation and 275 rpm, respectively. Culture pH was controlled at 7.0 by addition of $CO_2$ gas or 1 M $Na_2CO_3$. Culture temperature was maintained at 37° C. for the first 48 hours, and shifted to 33° C. thereafter. Process control in each bioreactor was achieved using a Digital Control Unit from B. Braun Biotech (Allentown, Pa.).

Sample Analyses

Antibody titer was determined using conventional protein A affinity chromatography with UV detection. See Fahrner et al., Biotechnol. Appl. Biochem. 30:121-128 (1999). Culture samples were analyzed for viable cell concentration and viability by Vi-Cell AS cell counter (Beckman Coulter, Fullerton, Calif.), pH and lactate by Bioprofile 400 bioanalyzer (Nova Biomedical, Waltham, Mass.), and osmolality by a multi-sample osmometer (Advanced Instruments, Norwood, Mass.).

Statistical Analysis

Two tailed student t-test was carried out using JMP software.

Results

Construction of a siRNA Vector Targeting PDHKs and LDHa

There are four PDHK genes reported by Harris et al. (*Adv. Enzyme Regul.* 42:249-59 (2002) in mammalian cells. To assess if all four PDHK genes present in CHO cells, four sets of RT-PCR primers were designed based on the conserved regions between human and mouse PDHK sequences. The PCR results revealed that even though all four PDHK mRNAs can be detected in CHO cells, PDHK4 mRNA level is minimal and much lower than other 3 PDHKs in DHFR-deficient (dihydrofolate reductase-deficient) CHO cells. Hence, only the expression of PDHK1, 2, and 3 genes was knocked down along with LDHa gene. For LDHa and each PDHK, three siRNA sequences were designed and tested in CHO cells to choose the siRNA sequence exhibiting best down-regulation of the target gene. The best siRNA sequence for LDHa was selected based on the findings by Kim and Lee. *Appl. Microbiol. Biotechnol.* 74(1):152-9 (2007). The siRNA sequence for LDHa and PDHKs were constructed in a single vector where siRNA for LDHa was under the control of U6 promoter, whereas siRNAs for each PDHK were driven by H1 promoters (FIG. 1).

Generation of Stable Clones with Reduced Expression of PDHK1, 2, 3, and LDHa

Figure 2:
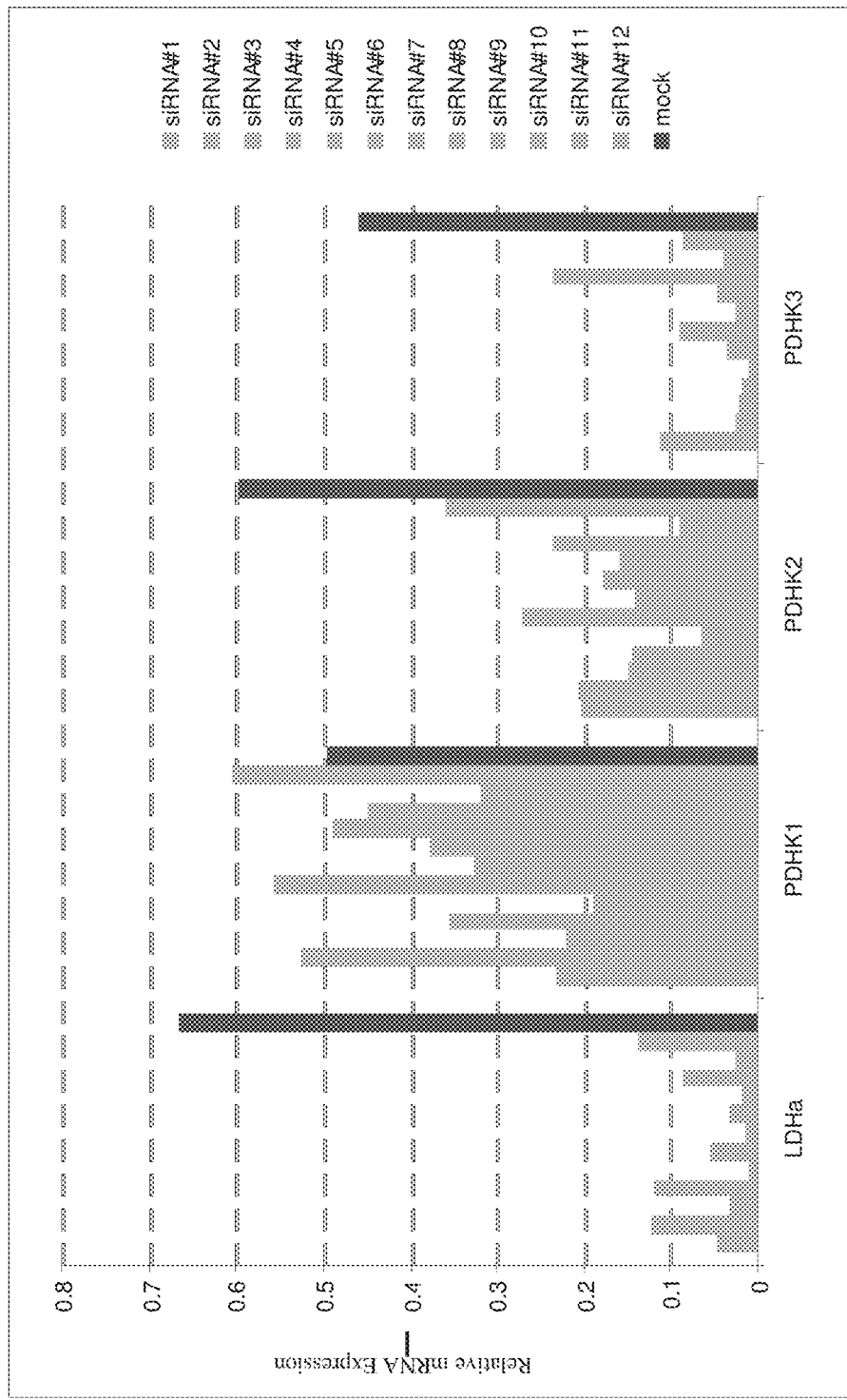
FIG. 2 shows relative LDHa, PDHK1, 2, and 3 mRNA expression levels in selected 12 siRNA clones (as shown in light gray color). Expression levels of LDHa and PDHKs were normalized to housekeeping gene b-microglobulin. The average mRNA expression levels from 12 mock clones were shown in dark gray color.

The siRNA construct targeting PDHKs and LDHa was transfected into CHO cells expressing a monoclonal antibody to get individual clones named siRNA clones. Individual siRNA clones were assayed for mRNA expression of four genes, PDHK1, 2, 3 and LDHa, using Taqman analysis. Twelve siRNA clones that exhibited most reduced expression of above four genes were identified (FIG. 2) for further analysis. The mock vector containing scramble sequence was also transfected into the same antibody expressing cells to get individual clones named mock clones. Twelve mock clones were chosen randomly as control and their mRNA expression levels of LDHa and PDHK1, 2, and 3 genes were also analyzed by Taqman. On average, the mRNA expression levels for LDHa, PDHK1, 2, and 3 in selected twelve siRNA clones were reduced by 90%, 32%, 83%, and 70% respectively compared to mock clones (FIG. 2).

Figure 3A:
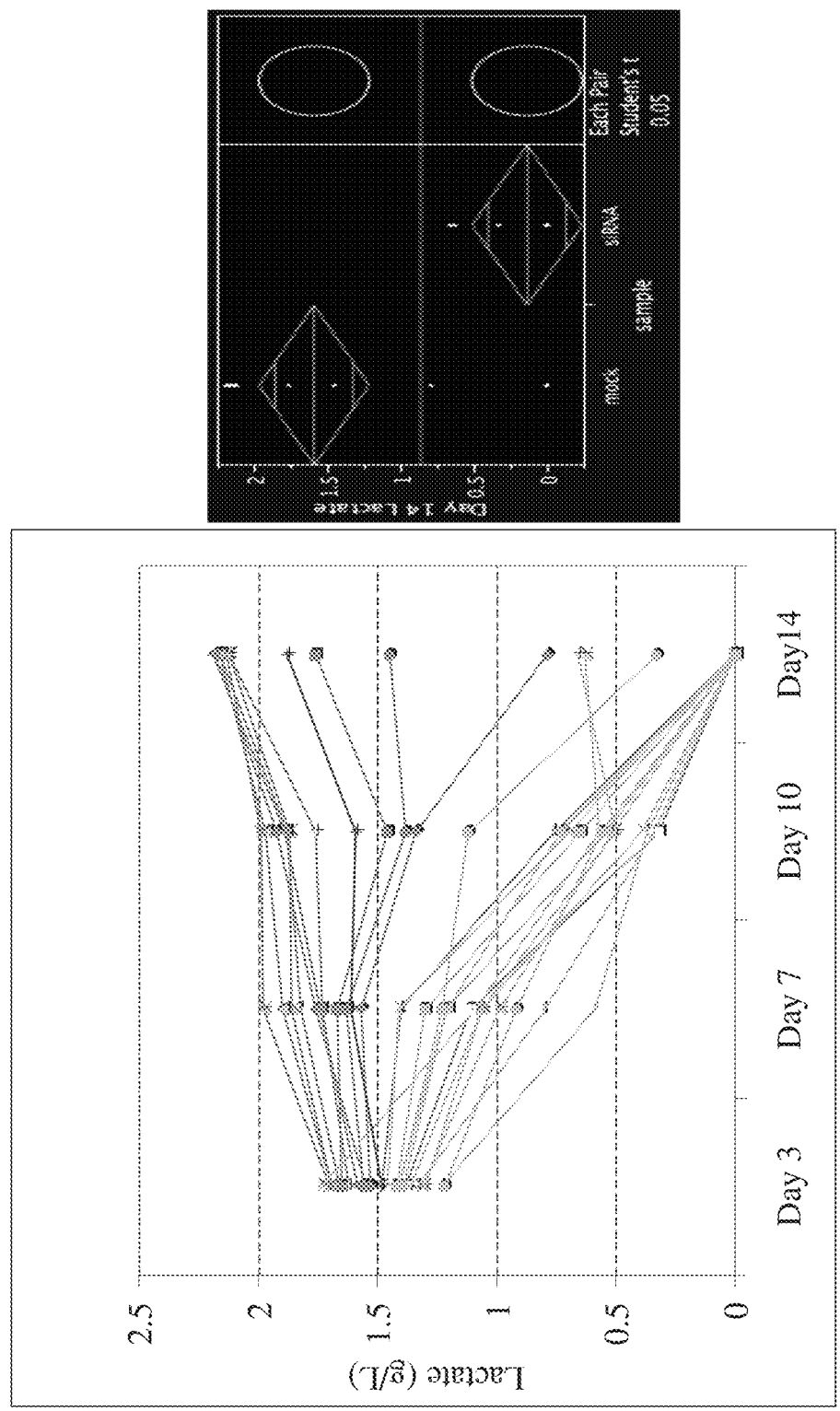
FIG. 3 shows lactate profiles, average lactate production rates, and day 14 pH values in fed-batch shake flask evaluation. Lactate concentrations were measured using Nova analyzer on day 3, 7, 10 and 14 during a 14-day shake flask evaluation. 3A). Lactate profile of mock (dark gray) and siRNA (light gray) clones; 3B). Average lactate production rate between days 3 and 14 (mg/$10^6$ cells/day); and 3C). Day 14 pH values. The fed-batch shake flask experiments were performed 3 times and the data shown is from 1 experiment.
Figure 3B:
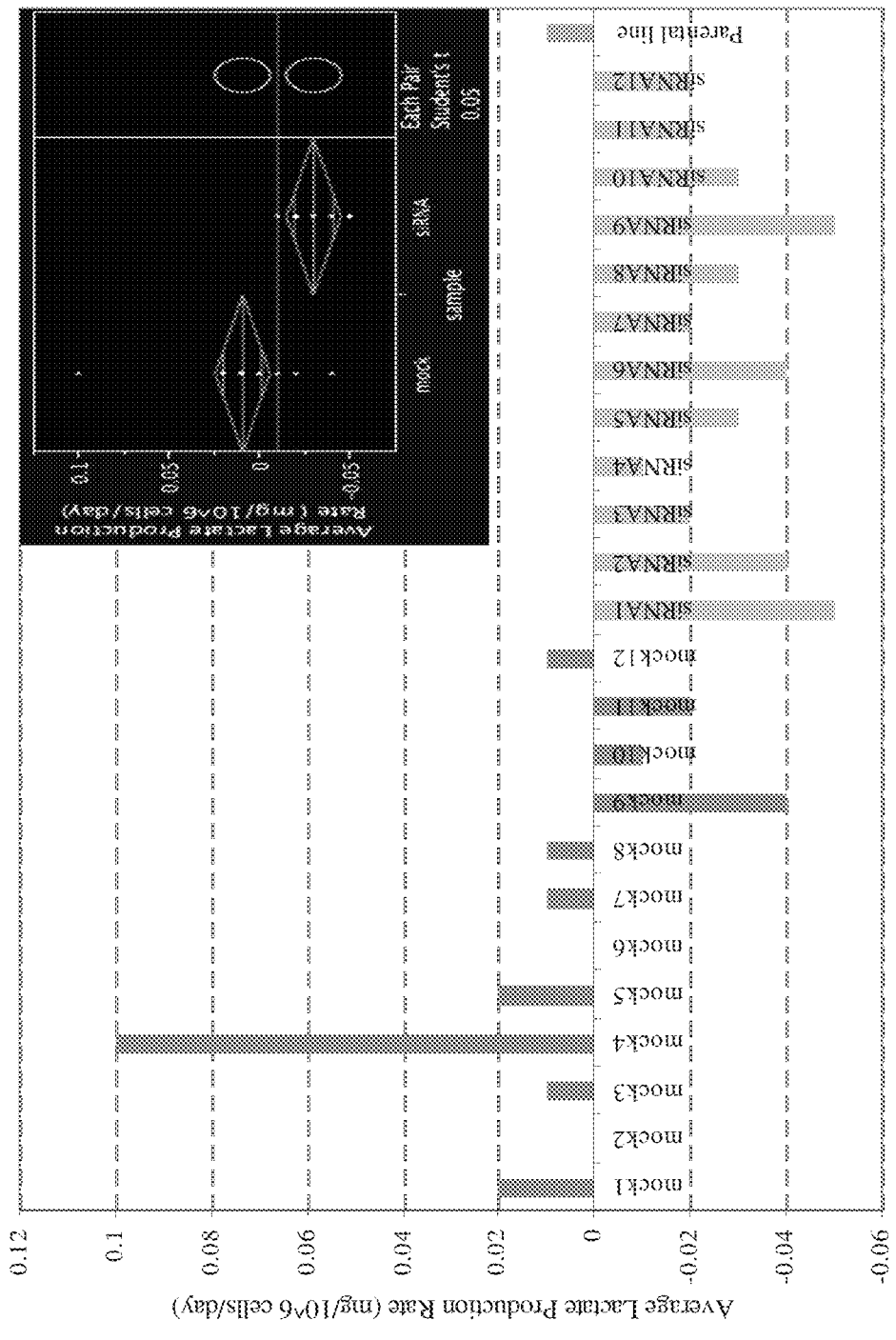
Figure 3C:
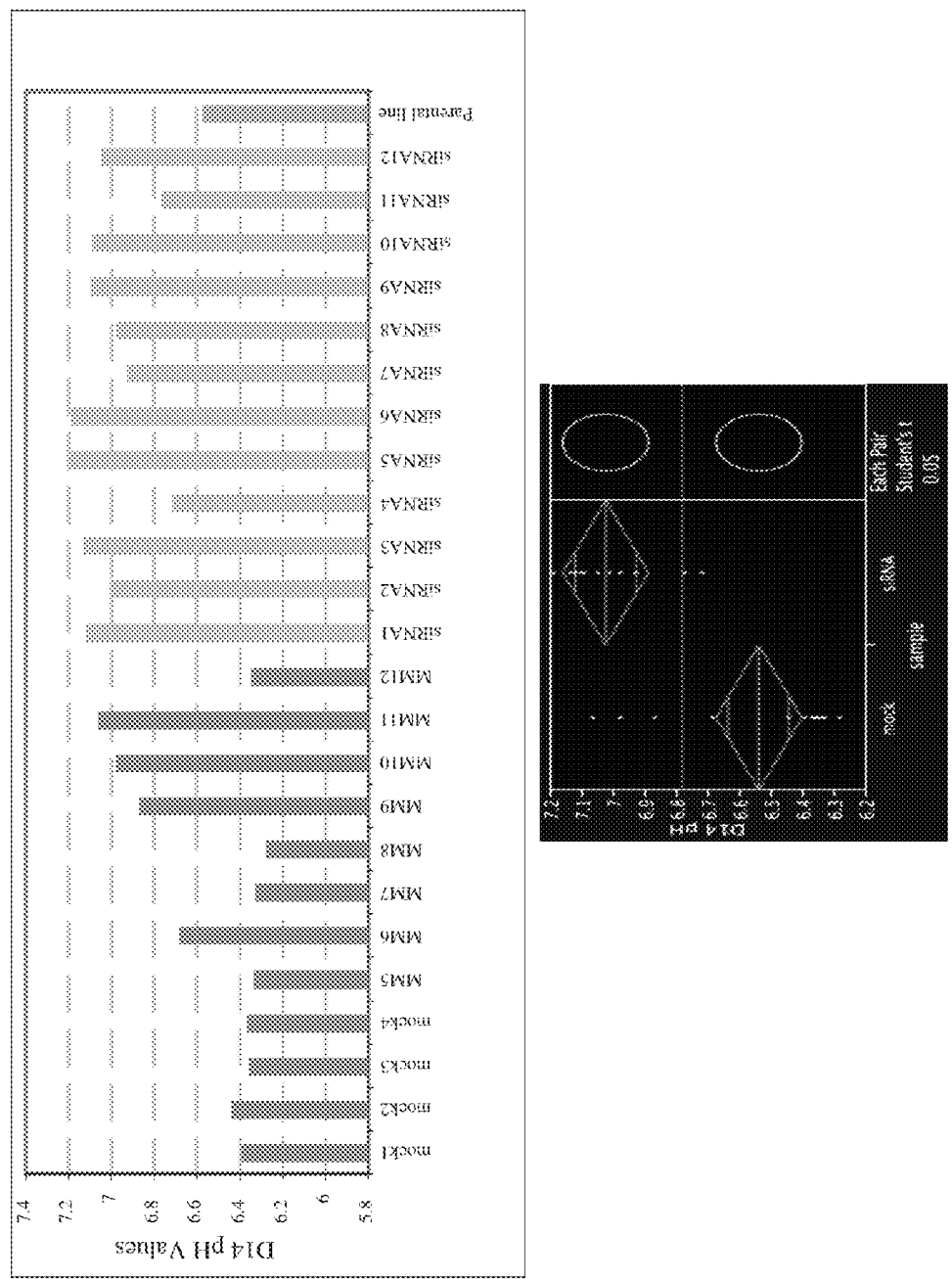
Figure 4A:
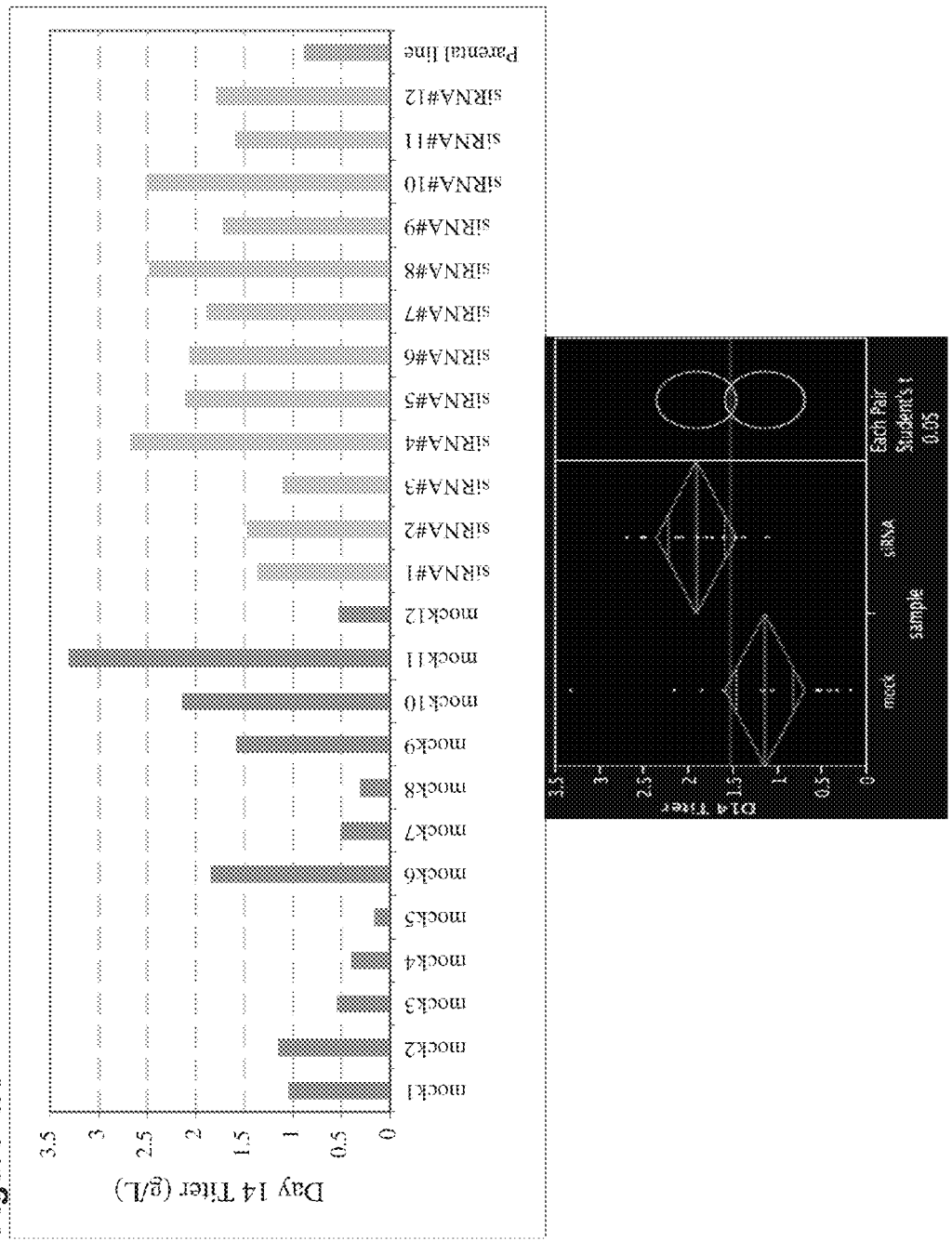
FIG. 4 shows titer, Specific Productivity (Qp) and cell growth profiles in fed-batch shake flask evaluation. 4A). Day 14 titer (productivity) in g/L; 4B). Specific Productivity in pg/cell/day; and 4C). Cell growth measure by integrated viable cell count (IVCC) in 100 millions of cells per day per liter. Mock clones are in dark gray and siRNA clones are in light gray.
Figure 4B:
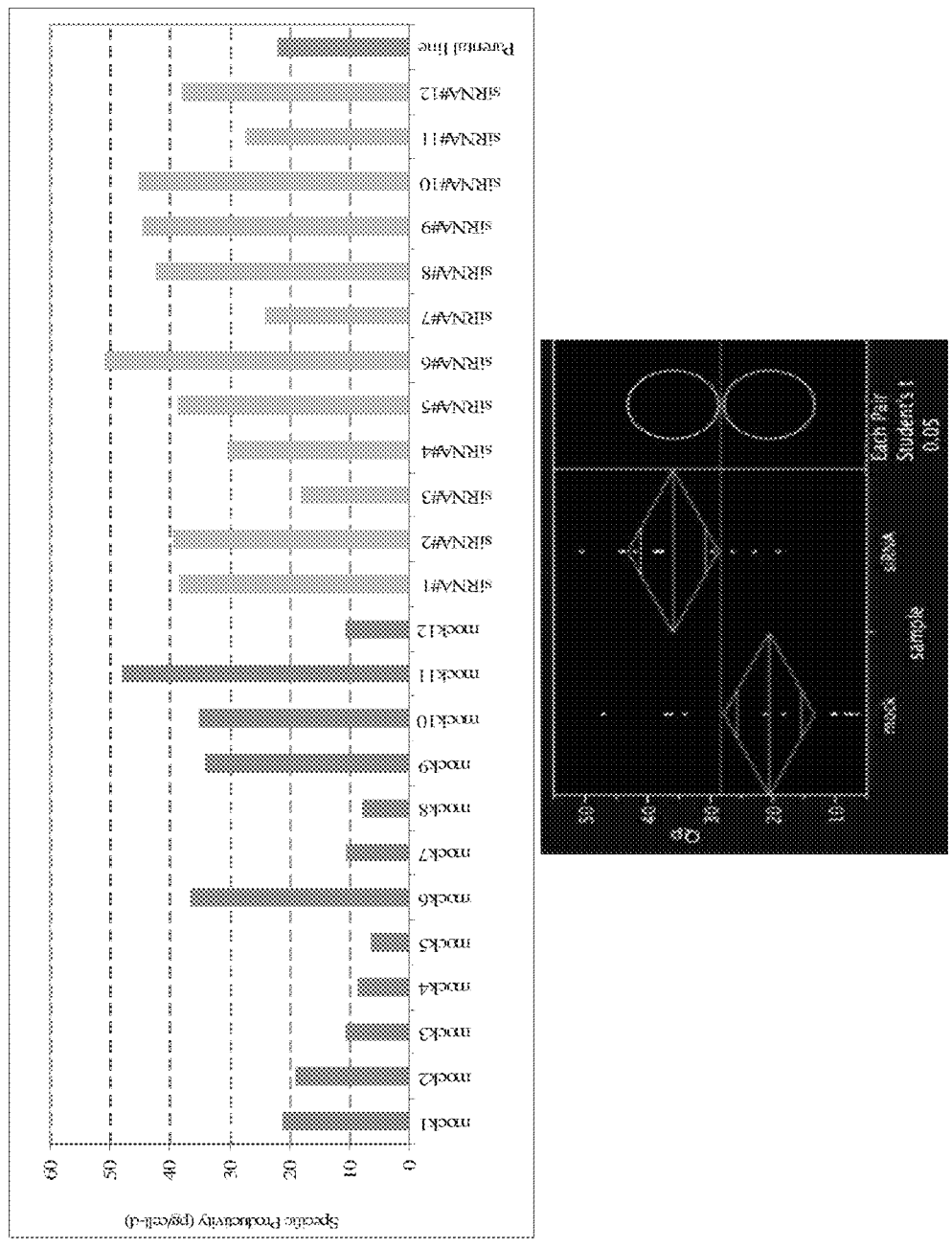

Fed-Batch Shake Flask Evaluation of siRNA and Mock Clones (a) Reduced Lactate Levels and Higher pHs in Culture Media Observed in siRNA Clones To evaluate the effect of siRNA-mediated down-regulation of LDHa and PDHKs on lactate production, 12 siRNA and 12 mock clones were evaluated in shake flask vessels in our proprietary medium employing a 14-day, fed-batch, and temperature shift process. The experiment has been repeated for three times and similar results were observed. The results from one set of experiment is shown as representatives in the figures. The results showed that compared to mock clones, siRNA clones had reduced lactate levels (FIG. 3) in general. By day 14, siRNA clones showed 91% less lactate in average than mock clones (p<0.0001) (FIG. 3A). Consistent with the lower lactate level in siRNA clones over the 14-day production period, the average lactate production rate for siRNA clones was negative 0.02 mg/$10^6$ cells/day, suggesting that lactate synthesis rate is lower than the consumption rate. In contrast, the average lactate production rate was 0.01 mg/$10^6$ cells/day for mock clones, indicating the overall lactate synthesis rate is higher than the consumption rate. This difference in lactate production rate between siRNA and mock clones was statistically significant (p<0.002) (FIG. 3B). Since lactate level in the media affects pH, by day 14, the average pH for mock clones dropped to 6.54, whereas the average pH for siRNA clones was 7.04 (FIG. 3C). The observed lower average pH is in agreement with higher average lactate level for mock clones.

b) Increased Antibody Titer and Specific Productivity (Qp) Observed in siRNA Clones To investigate whether knocking down gene expression of PDHKs and LDHa affect antibody production, samples were collected from fed-batch shake flask experiments on day 3, 7, 10 and 14 to measure antibody titers by protein A chromatography. The data showed that, on average, siRNA clones produced 68% more antibody that that of mock clones (FIG. 4A, p<0.022), and average cell-specific productivity (Qp) measured in pg/cell-d for siRNA clones was 75% higher than that for mock clones (FIG. 4B, p<0.006). To evaluate cell growth, shake flask samples were collected on day 3, 7, 10, and 14 to measure viable cell counts and viabilities to calculate integrated viable cell count (IVCC). In contrast to antibody titers and Qps, no appreciable cell growth differences were observed between the two groups (FIG. 4C). Antibody product quality attributes including glycan profile, charge variants and percentage of aggregation were comparable between siRNA and mock clones.

Bioreactor Fed-Batch Culture Evaluation of siRNA Mock Clones

Figure 5B:
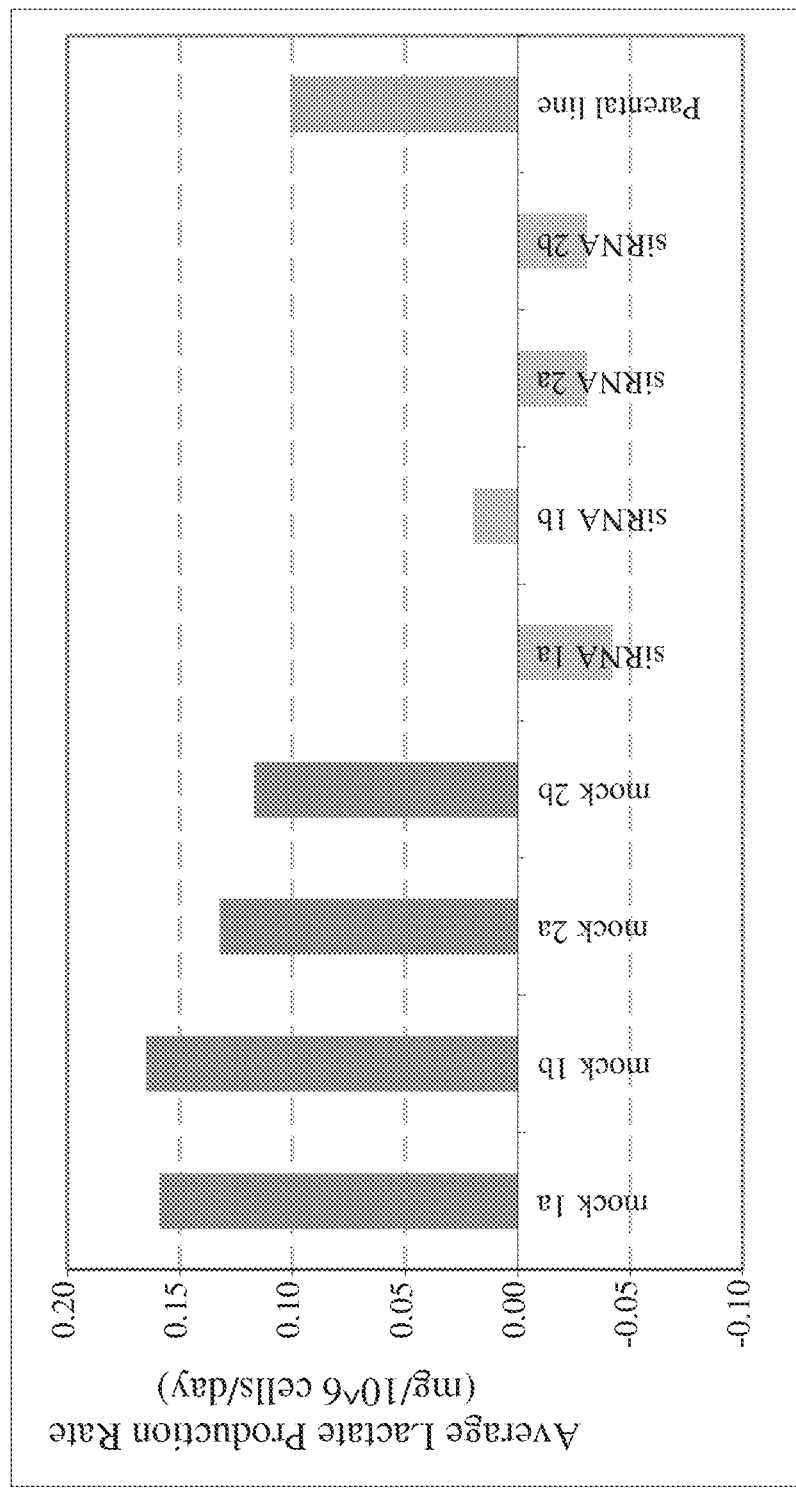
FIG. 5 shows lactate profile, average lactate production rates, and osmolality profile in 2 L bioreactor evaluations. 5A). Lactate profile; 5B). Average lactate production rates; and 5C). Osmolality profile.
Figure 5C:
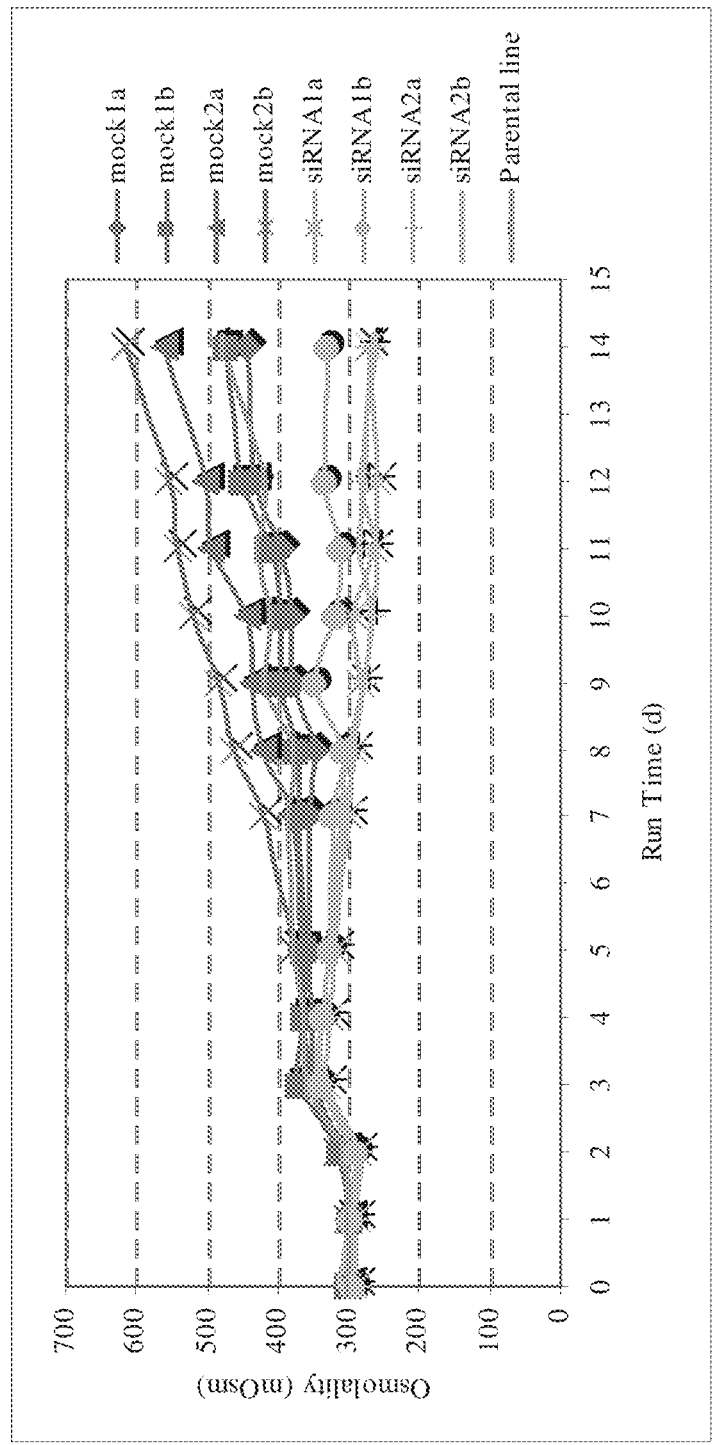
Figure 6:
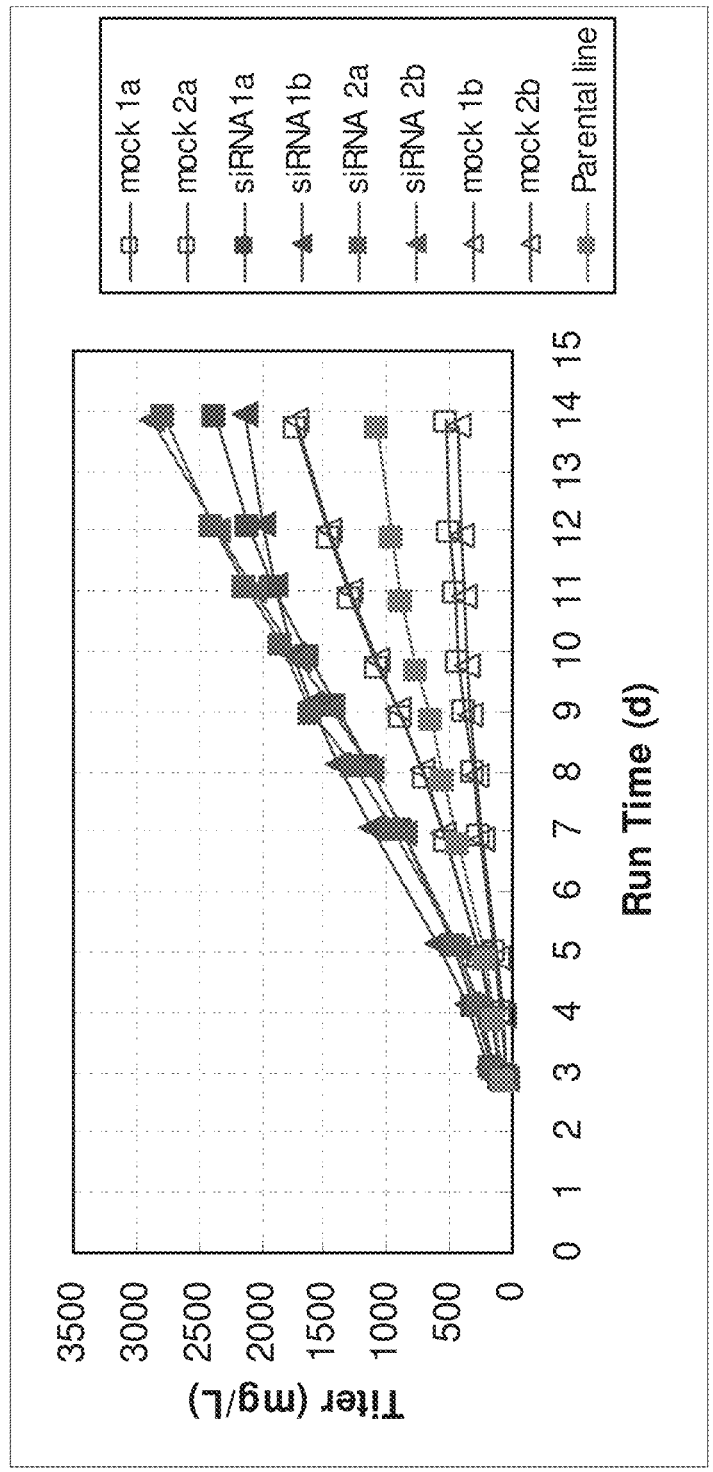
FIG. 6 shows productivity profile of cultured cells containing siRNA, mock, or parent clones in 2 L bioreactor evaluation.

Since pH-controlled fed-batch bioreactor culture is the standard scale-down model for large scale manufacturing, the performance of some siRNA and mock clones in 2 L bioreactors was further investigated. Given the limitation in bioreactor availability and experimental complexity, 12 siRNA and 12 mock clones in duplicates were not run due to impracticability. Two representative siRNA clones and two representative mock clones whose metabolic profiles best represented the average performance for each group to minimize selection bias, along with the parental line used for siRNA and mock plasmid transfections for 2 L bioreactor evaluation were selected. Cell culture samples were collected daily (except on days 6 and 13) for lactate, glucose, osmolality, and titer analysis. The lactate levels for siRNA clones generally remained flat whereas the lactate levels for mock and parental clones continued to increase during the 14-day production period. On day 14, the two siRNA clones had 86% lower lactate level on average in media than mock clones or parental clone (FIG. 5A) and had lower specific lactate production rate than mock clones and parent line (FIG. 5B). Similarly, the osmolarities for siRNA clones remained around 300 mOsm whereas the osmolarities for mock clones or parental clone continued to increase during the 14-day production period. On day 14, average osmolarities for 2 siRNA clones were 60% lower than those of mock and parent clones (FIG. 5C). Importantly, on day 14, the siRNA clones on average produced 125% more antibody than that of mock clones (FIG. 6). As observed in fed-batch shake flask evaluation, siRNA and mock clones have comparable viabilities and cell growth in 2 L bioreactors.

Discussion

Previous study demonstrated that down-regulating LDHa gene expression alone was able to reduce lactate production. Kim and Lee, *Appl. Microbiol. Biotechnol.* 74(1):152-9 (2007). However, in their study despite the 45-79% reduction in lactate level, there was no significant improvement in Qp and product titer suggesting that knocking down LDHa alone in CHO cells is not sufficient to improve Qp and product yield efficiently. Further, simultaneously down-regulating PDHK1, 2, and 3 in CHO cells was neither sufficient to reduce lactate level nor to increase antibody productivity. Since the only way for cells to generate lactate is through pyruvate reduction, and pyruvate can not only be converted to lactate by LDH but also be converted to acetyl-CoA by PDH entering TCA cycle to be oxidized, reducing lactate production by knocking down LDHa expression and promoting pyruvate into TCA cycle by knocking down PDHKs may synergize to reduce lactate level and to provide cells with more energy and possibly metabolic intermediates leading to increased antibody production.

The expression of LDHa, PDHK2, and PDHK3 was substantially reduced and the expression of PDHK1 was moderately reduced in all clones tested. The moderate reduction in PDHK1 expression is likely due to non-optimum siRNA targeting sequence since moderate reduction was observed with three PDHK1 siRNA sequences tested. Variations on lactate production and antibody production in mock and siRNA clones were observed, since each clone had different expression levels of LDHa and PDHKs. Nevertheless, by day 14, the average lactate level in siRNA group was lower than that in mock group leading to the lower average pH for mock clones than that of siRNA clones in fed-batch shake flask culture. More importantly, in addition to lower specific lactate production rate, the average titer and Qp for siRNA clones increased by 68% and 75% respectively compared to those of mock clones with no noticeable differences in cell growth and product quality between siRNA and mock clones. Interestingly, for the day 14 titers versus day 14 lactate levels, there was a good inverse relationship between titers and lactate levels among mock clones, but not among siRNA clones. The observed differences in titers and lactate levels among mock clones may be likely that parental clone is heterogeneous in antibody productivity and cellular metabolism even though the cell line was derived from a single clone. A total of 12 mock clones were evaluated to take into consideration of clonal variation. The data indicate that knocking down LDHa and PDHKs simultaneously reduces lactate level and improves antibody production in CHO cells. Hence, for the development of robust and productive antibody production processes, simultaneous down regulation of both LDHa and PDHKs provides an efficient approach.

The performance of 2 mock and 2 siRNA clones in 2 L bioreactors with duplicates was further investigated. Those 4 clones were selected to best represent the average productivity in each group based on fed-batch shake flask evaluations. Similar to the observations from shake flask experiment, the siRNA clones had lower lactate levels and higher titers than mock clones in 2 L bioreactor evaluation. Given that pH is controlled in fed-batch 2 L bioreactors, the mock cultures exhibited increased osmolality than siRNA cultures since higher lactate levels in mock clones needed more alkali addition to maintain set point pH.

In summary, the data from fed-batch shake flask and 2 L bioreactor evaluations demonstrated that simultaneous knockdown of LDHa, PDHK1, 2, and 3 in CHO cells is effective in reducing lactate level and in increasing antibody titer without impacting cell growth and product quality.

What is claimed is:

1. A method for reducing lactate production in cultured cells, the method comprising culturing cells comprising a first heterologous nucleic acid sequence encoding a small interfering RNA (siRNA) specific for a lactate dehydrogenase (LDH) and a second heterologous nucleic acid sequence encoding an siRNA specific for a pyruvate dehydrogenase kinase (PDHK), wherein the first heterologous nucleic acid sequence is operably linked to a first promoter, and wherein the second heterologous nucleic acid sequence is operably linked to a second promoter, wherein the cultured cells have a polypeptide productivity of at least about 68% higher than cultured cells without the heterologous nucleic acid sequence comprising siRNA specific for PDHK and the siRNA specific for LDH.

2. The method of claim 1, wherein the LDH is LDHa.

3. The method of claim 1, wherein the cultured cells further comprise a third heterologous nucleic acid sequence encoding an siRNA specific for a second PDHK and wherein the third heterologous nucleic acid sequence is operably linked to a third promoter.

4. The method of claim 3, wherein the cultured cells further comprise a fourth heterologous nucleic acid sequence encoding an siRNA specific for a third PDHK and wherein the fourth heterologous nucleic acid sequence is operably linked to a fourth promoter.

5. The method of claim 4, wherein cultured cells further comprise a fifth heterologous nucleic acid sequence encoding an siRNA specific for a fourth PDHK and wherein the fifth heterologous nucleic acid sequence is operably linked to a fifth promoter.

6. The method of any one of claims 1, 3, 4, and 5, wherein the PDHK is selected from the group consisting of PDHK1, PDHK2, PDHK3, and PDHK4.

7. The method of claim 1, wherein the cultured cells produce a heterologous polypeptide.

8. The method of claim 7, wherein the heterologous polypeptide is an antibody.

9. The method of claim 4, wherein an average lactate production rate of the cultured cells is less than about negative 0.02 mg/$10^6$ cells/day.

10. The method of claim 4, wherein the cultured cells have a Specific Productivity of at least about 75% higher than cultured cells without the heterologous nucleic acid sequence comprising the siRNA specific for PDHKs and the siRNA specific for LDH.

11. The method of claim 4, wherein the cultured cells maintain an osmolality at less than about 300 mOsm over 14 days.

12. The method of claim 7, wherein the cultured cells are mammalian cells.

* * * * *

```
                            SEQUENCE LISTING

<160> NUMBER OF SEQ ID NOS: 19

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
ctcgattccg ttatctgat                                                  19

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
gcagttcctg gacttcgga                                                  19

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
cattcagtac ttcttggac                                                  19

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
tgtagctgat gtcgtgaaa                                                  19

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct
```

<400> SEQUENCE: 5
gcccatctca tcgaaaaca                                                19

<210> SEQ ID NO 6
<211> LENGTH: 25
<212> TYPE: DNA
<213> ORGANISM: Artificial Sequence
<220> FEATURE:
<223> OTHER INFORMATION: Synthetic Construct

<400> SEQUENCE: 6
agccatcttt aatgacttcg actac                                         25

<210> SEQ ID NO 7
<211> LENGTH: 27
<212> TYPE: DNA
<213> ORGANISM: Artificial Sequence
<220> FEATURE:
<223> OTHER INFORMATION: Synthetic Construct

<400> SEQUENCE: 7
tcgcagtttg gatttatgct tccaatg                                       27

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct

<400> SEQUENCE: 8
gatctgtcca tcaaaatgag tga                                           23

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
tgtggagtac atgtagctga aga                                           23

<210> SEQ ID NO 10
<211> LENGTH: 26
<212> TYPE: DNA
<213> ORGANISM: Artificial Sequence
<220> FEATURE:
<223> OTHER INFORMATION: Synthetic Construct

<400> SEQUENCE: 10
ctctcaatct tcctcaaggg gacacc                                        26

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
cagcctggag cctacaaga                                                19

```
<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
ggcatacagt cgagaaattg g                                              21

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13
aagccataac caaatccagc caagg                                          25

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
gccgagagca taatgaagaa                                                20

<210> SEQ ID NO 15
<211> LENGTH: 24
<212> TYPE: DNA
<213> ORGANISM: Artificial Sequence
<220> FEATURE:
<223> OTHER INFORMATION: Synthetic Construct

<400> SEQUENCE: 15
ccatagagac ccttaatcat ggta                                           24

<210> SEQ ID NO 16
<211> LENGTH: 22
<212> TYPE: DNA
<213> ORGANISM: Artificial Sequence
<220> FEATURE:
<223> OTHER INFORMATION: Synthetic Construct

<400> SEQUENCE: 16
cttaggcggg tgcatcccat tt                                             22

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
tcctctcagt ggtctgcttg g                                              21

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct
```

```
<400> SEQUENCE: 18
tggcgtgtgt agacttgcac tt                                           22

<210> SEQ ID NO 19
<211> LENGTH: 19
<212> TYPE: DNA
<213> ORGANISM: Artificial Sequence
<220> FEATURE:
<223> OTHER INFORMATION: Synthetic Construct

<400> SEQUENCE: 19
tgccatccag cgtccccca                                               19
```